(12) United States Patent
Allen et al.

(10) Patent No.: US 8,252,529 B2
(45) Date of Patent: Aug. 28, 2012

(54) METHODS FOR COLLECTING AND DETECTING OLIGONUCLEOTIDES

(75) Inventors: Paul G. Allen, Seattle, WA (US); Edward S. Boyden, Cambridge, MA (US); Roderick A. Hyde, Redmond, WA (US); Muriel Y. Ishikawa, Livermore, CA (US); Stephen L. Malaska, Redmond, WA (US); Dennis J. Rivet, Portsmouth, VA (US); Leif T. Stordal, Issaquah, WA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 364 days.

(21) Appl. No.: 12/157,985

(22) Filed: Jun. 12, 2008

(65) Prior Publication Data

US 2009/0311269 A1 Dec. 17, 2009

(51) Int. Cl.
*C12Q 1/68* (2006.01)
*C07H 21/04* (2006.01)
*C07H 21/02* (2006.01)
*C07K 14/00* (2006.01)
*C07K 16/00* (2006.01)

(52) U.S. Cl. ....... 435/6; 536/23.1; 536/24.3; 536/24.31; 536/24.33; 536/24.5; 530/350; 530/387.1

(58) Field of Classification Search .................. None
See application file for complete search history.

(56) References Cited

U.S. PATENT DOCUMENTS

| | | | |
|---|---|---|---|
| 4,966,964 A | 10/1990 | Shapiro et al. | |
| 5,019,556 A | 5/1991 | Shapiro et al. | |
| 5,155,018 A | 10/1992 | Gillespie et al. | |
| 5,266,687 A | 11/1993 | Shapiro et al. | |
| 5,734,039 A | 3/1998 | Calabretta et al. | |
| 6,329,179 B1 | 12/2001 | Kopreski | |
| 6,465,195 B1 | 10/2002 | Holtzman et al. | |
| 6,607,898 B1 | 8/2003 | Kopreski et al. | |
| 6,630,301 B1 | 10/2003 | Gocke et al. | |
| 6,663,846 B1 | 12/2003 | McCombs et al. | |
| 6,759,217 B2 | 7/2004 | Kopreski | |
| 6,794,135 B1 | 9/2004 | Kopreski et al. | |
| 6,916,634 B2 | 7/2005 | Kopreski | |
| 7,256,003 B2 | 8/2007 | Iqbal et al. | |
| 2002/0106684 A1 | 8/2002 | Kopreski | |
| 2002/0155469 A1 | 10/2002 | Kopreski | |
| 2003/0026841 A1 | 2/2003 | Trubetskoy et al. | |
| 2003/0036068 A1 | 2/2003 | Kopreski | |
| 2003/0044829 A1 | 3/2003 | Kopreski | |
| 2003/0087276 A1 | 5/2003 | Kopreski | |
| 2003/0104454 A1 | 6/2003 | Kopreski | |
| 2004/0014079 A1 | 1/2004 | Kopreski et al. | |
| 2004/0132019 A1 | 7/2004 | Chen et al. | |
| 2004/0171021 A1 | 9/2004 | Siegler | |
| 2004/0220081 A1 | 11/2004 | Kreitz et al. | |
| 2004/0247680 A1 | 12/2004 | Farokhzad et al. | |
| 2005/0003440 A1 | 1/2005 | Kopreski | |
| 2005/0032063 A1 | 2/2005 | Kopreski | |
| 2005/0070489 A1 | 3/2005 | Carter et al. | |
| 2005/0106152 A1 | 5/2005 | Hikichi et al. | |
| 2005/0260594 A1 | 11/2005 | Kopreski et al. | |
| 2005/0266405 A1 | 12/2005 | Kopreski | |
| 2006/0166229 A1 | 7/2006 | Kopreski | |
| 2006/0172321 A1 | 8/2006 | Gocke et al. | |
| 2006/0204956 A1 | 9/2006 | Kopreski et al. | |
| 2006/0204989 A1 | 9/2006 | Kopreski | |
| 2006/0228729 A1 | 10/2006 | Kopreski | |
| 2006/0228732 A1 | 10/2006 | Kopreski | |
| 2006/0286578 A1 | 12/2006 | Kopreski et al. | |
| 2007/0009934 A1 | 1/2007 | Kopreski | |
| 2007/0026427 A1 | 2/2007 | Kopreski | |
| 2007/0032418 A1 | 2/2007 | Shapiro et al. | |
| 2007/0099203 A1 | 5/2007 | Zhang | |
| 2008/0050783 A1 | 2/2008 | Kopreski | |
| 2008/0057502 A1 | 3/2008 | Kopreski | |
| 2009/0291438 A1 | 11/2009 | Kopreski | |

OTHER PUBLICATIONS

Nielsen (Exp Opin Invest Drugs, 2001, 10(2), pp. 331-341).*
Larsen et al. (Biochemica et Biophsyica Acta, 1489, 1999, pp. 159-166.*
Qadota et al.; "Establishment of a tissue-specific RNAi system in *C. elegans*"; Gene; 2007; pp. 166-173; vol. 400; Elsevier B. V.
Welker et al.; "Genes misregulated in *C. elegans* deficient in Dicer, RDE-4, or RDE-1 are enriched for innate immunity genes"; RNA; 2007; pp. 1090-1102; vol. 13; No. 7; Cold Spring Harbor Laboratory Press.
Zamecnik et al.; "Inhibition of Rous sarcoma virus replication and cell transformation by a specific oligodeoxynucleotide"; Proc. Natl. Acad. Sci. USA; Jan. 1978; pp. 280-284; vol. 75; No. 1.
Cerritelli, Susana M. et al.; "Failure to Produce Mitochondrial DNA Results in Embryonic Lethality in Rnasehl Null Mice"; Molecular Cell; Mar. 2003; pp. 807-815; vol. 11; Cell Press.
Matzke, Marjori A. et al.; "RNAi-Mediated Pathways in the Nucleus"; Nature Reviews/ Genetics; Jan. 2005; pp. 24-35; vol. 6; Nature Publishing Group.

(Continued)

*Primary Examiner* — Amy Bowman

(57) ABSTRACT

Methods, pharmaceutical compositions, and kits are provided which includes accurately sampling a RNA from a tissue of an animal and analyzing RNA in the tissue of the animal as an indicator of physiological state, infectious disease, neoplastic disease, autoimmune disease, inflammatory disease, cardiovascular disease, atherosclerotic disease, or neurological disease in the animal. A method is provided which includes administering at least one compound to an animal wherein the at least one compound is configured to prevent the cleavage of at least one tissue RNA by a ribonuclease. The method further includes collecting a sample of at least a portion of tissue from the animal.

44 Claims, 13 Drawing Sheets

OTHER PUBLICATIONS

Allard et al.; "Park7 and Nucleoside Diphosphate Kinase A as Plasma Markers for the Early Diagnosis of Stroke"; Clinical Chemistry; 2005; pp. 2043-2051; vol. 51, Issue No. 11; American Association for Clinical Chemistry.

Azarani, Arezou; Hecker, Karl H.; "RNA analysis by ion-pair reversed-phase high performance liquid chromatography"; Nucleic Acids Research; 2001; pp. 1-9; vol. 29, No. 2; Oxford University Press.

Barad et al.; "MicroRNA expression detected by oligonucleotide microarrays: System establishment and expression profiling in human tissues"; Genome Research; 2004; pp. 2486-2494; vol. 14; Cold Springs Harbor Laboratory Press.

Barreau et al.; "Survey and Summary, AU-rich elements and associated factors: are there unifying principles?"; Nucleic Acids Research; 2005; pp. 7138-7150; vol. 33, No. 22; Oxford University Press.

Becker et al.; "Markers and Tissue Resources for Melanoma: Meeting Report"; Nov. 15, 2006; pp. 10652-10657; vol. 66, No. 22; American Association for Cancer Research.

Beintema, J. J.; Kleineidam, R. G.; "The ribonuclease A superfamily: general discussion"; CMLS Cellular and Molecular Life Sciences; 1998; pp. 825-832; vol. 54; Birkhäuser Verlag, Basel.

Beld et al.; "Low Levels of Hepatitis C Virus RNA in Serum, Plasma, and Peripheral Blood Mononuclear Cells of Injecting Drug Users During Long Antibody-Undetectable Periods Before Seroconversion"; Blood; Aug. 15, 1999; pp. 1183-1191; vol. 94, No. 4; The American Society of Hematology.

Benson et al.; "GenBank"; Nucleic Acids Research; Dec. 11, 2007 and 2008; pp. D25-D30; vol. 36; The Author(s).

Betel et al.; "The microRNA.org resource: targets and expression"; Nucleic Acids Research; 2008; pp. D149-D153; vol. 36; The Author(s).

Bielekova, Bibiana; Martin, Roland; "Review Article, Development of biomarkers in multiple sclerosis"; Brain; 2004; pp. 1463-1478; vol. 127, No. 7; Guarantors of Brain.

Boyle, MD et al.; "Tyrosinase Expression in Malignant Melanoma, Desmoplastic Melanoma, and Peripheral Nerve Tumors, an Immunohistochemical Study"; Arch Pathol Lab Med; Jul. 2002; pp. 816-822; vol. 126.

Cao et al.; "Molecular Beacon Aptamers for Protein Monitoring in Real-Time and in Homogenous Solutions"; Current Proteomics; 2005; pp. 31-40; vol. 2, No. 1; Bentham Science Publishers, Ltd.

Chirgwin et al.; "Isolation of Biologically Active Ribonucleic Acid from Sources Enriched Ribonuclease"; Biochemistry; 1979; pp. 5294-5299; vol. 18, No. 24; American Chemical Society.

Chiu et al.; "Time Profile of Appearance and Disappearance of Circulating Placenta-Derived mRNA in Maternal Plasma"; Clinical Chemistry; 2006; pp. 313-316; vol. 53, No. 2.

Denkert et al.; "Expression of the ELAV-Like Protein HuR Is Associated with Higher Tumor Grade and Increased Cyclooxygenase-2 Expression in Human Breast Carcinoma"; Clinical Cancer Research; Aug. 15, 2004; pp. 5580-5586; vol. 10.

Denkert et al.; "Expression of the ELAV-like protein HuR in human colon cancer: association with tumor stage and cyclooxyenase-2"; Modern Pathology; 2006; pp. 1261-1269; vol. 19; USCAP, Inc.

Dickman, Mark J.; Hornby, David P.; "Enrichment and analysis of RNA centered on ion pair reverse phase methodology"; RNA; 2006; pp. 691-696; vol. 12, No. 4; Cold Spring Harbor Laboratory Press, RNA Society.

Eisenberg, Eli; Levanon, Erez Y.; "Human housekeeping genes are compact"; Trends in Genetics; Jul. 2003; pp. 362-365; vol. 19, No. 7.

El-Hefnawy et al.; "Characterization of Amplifiable, Circulating, RNA in Plasma and Its Potential as a Tool for Cancer Diagnostics"; Clinical Chemistry, Cancer Diagnostics; 2004; pp. 564-573; vol. 50, No. 3.

Fach et al.; "In Vitro Biomarker Discovery for Atherosclerosis by Proteomics"; Molecular & Cellular Proteomics; 2004; pp. 1200-1210; vol. 3, No. 12; The American Society for Biochemistry and Molecular Biology, Inc.

Gabig-Ciminska, Magdalena; "Microbial Cell Factories, Review, Developing nucleic acid-based electrical detection systems"; BioMed Central; 2006; pp. 1-8; vol. 5, No. 9; Gabig-Ciminska; licensee BioMed Central Ltd.

Gedela et al.; "Indentification of Biomarkers for Type 2 Diabetes and Its Complications: A Bioinformatic Approach"; International Journal of Biomedical Science; Dec. 2007; pp. 229-236; vol. 3, No. 4.

Gill et al.; "Nucleic Acid Isothermal Amplification Technologies—A Review"; *Nucleosides, Nucleotides, and Nucleic Acids*; 2008; pp. 224-243; vol. 27; Taylor & Francis Group, LLC.

Godfrey et al.; "Prognostic Value of Quantitative Reverse Transcription-Polymerase Chain Reaction in Lymph Node-negative Esophageal Cancer Patients[1]"; Clinical Cancer Research, Molecular Detection of Micrometastases; Dec. 2001; pp. 4041-4048; vol. 7.

Grossman et al.; "The Use of Urine-Based Biomarkers in Bladder Cancer"; Urology; Mar. 2006; pp. 62-64; vol. 67; Elsevier Inc.

Hamaoui et al.; "Concentration of Circulating Rhodopsin mRNA in Diabetic Retinopathy"; Clinical Chemistry, Technical Briefs; 2004; pp. 2152-2155; vol. 50, No. 11.

Hanke et al.; "CEA and CA 19-9 measurement as a monitoring parameter in metastatic colorectal cancer (CRC) under palliative first-line chemotherapy with weekly 24-hour infusion of high-dose 5-fluorouracil (5-FU) and folinic acid (FA)"; Annals of Oncology; 2001; pp. 221-226; vol. 12; Kluwer Academic Publishers, Printed in the Netherlands.

Hanke et al.; "Detailed Technical Analysis of Urine RNA-Based Tumor Diagnostics Reveals ETS2/Urokinase Plasminogen Activator to Be a Novel Marker for Bladder Cancer"; Clinical Chemistry, Molecular Diagnostics and Genetics; 2007; pp. 2070-2077; vol. 53, No. 12; American Association for Clinical Chemistry.

Hasselmann et al.; "Extracellular Tyrosinase mRNA within Apoptotic Bodies Is Protected from Degradation in Human Serum"; Clinical Chemistry, Technical Briefs; 2001; pp. 1488-1489; vol. 47, No. 8.

Johnson, Philip J.; Lo, Y.M. Dennis; "Plasma Nucleic Acids in the Diagnosis and Management of Malignant Disease"; Clinical Chemistry, Cancer Diagnostics: Review; 2002; pp. 1186-1193; vol. 48, No. 8; American Association for Clinical Chemistry.

Kanneganti et al.; "Bacterial RNA and small antiviral compounds activate caspase-1 through cryopyrin/Nalp3"; Nature; Mar. 9, 2006; pp. 233-236; vol. 440; Nature Publishing Group.

Icao et al.; "A small-molecule inhibitor of the ribonucleolytic activity of human angiogenin that possesses antitumor activity"; PNAS, Medical Sciences; Jul. 23, 2002; pp. 10066-10071; vol. 99, No. 15.

Karlsson et al.; "Retroviral RNA identified in the cerebrospinal fluids and brains of individuals with schizophrenia"; PNAS, Medical Sciences; Apr. 10, 2001; pp. 4634-4639; vol. 98, No. 8.

Kimoto et al.; "Cellular response to the ribonuclease injection; a morphologic and cytochemical study"; Acta Med.; 1960; pp. 77-103; vol. 14, Issue 2; Okayama University Medical School.

Kinasewitz et al.; "Research, Universal changes in biomarkers of coagulation and inflammation occur in patients with severe sepsis, regardless of causative microorganism [ISRCTN74215569]"; Critical Care, Open Access; Apr. 2004; pp. R82-R90; vol. 8, No. 2.

Kopreski et al.; "Advances in Brief, Detection of Tumor Messenger RNA in the Serum of Patients with Malignant Melanoma"; Clinical Cancer Research; Aug. 1999; pp. 1961-1965; vol. 5.

Kubo et al.; "Rapid Communication, Detection of WTI mRNA in urine from patients with kidney diseases"; European Journal of Clinical Investigation; 1999; pp. 824-826; vol. 29; Blackwell Science Ltd.

La Coste et al.; "Somatic mutations of the β-catenin gene are frequent in mouse and human hepatocellular carcinomas"; Proc. Natl. Acad. Sci. USA; Jul. 1998; pp. 8847-8851; vol. 95; The National Academy of Sciences.

Lai et al.; "A Simplified Method for PCR Detection of Hepatitis C Virus RNA from Human Serum"; PCR Methods and Applications, Technical Tips; 1994; pp. 308-309; vol. 3; Cold Spring Harbor Laboratory Press.

Lazar, James G.; "Advanced Methods in PCR Product Detection"; PCR Methods and Applications, Manual Supplement; 1994; pp. S1-14; vol. 4; Cold Spring Harbor Laboratory.

Li et al.; "Serum Circulating Human mRNA Profiling and Its Utility for Oral Cancer Detection"; Journal of Clinical Oncology, Original Report; Apr. 10, 2006; pp. 1754-1760; vol. 24, No. 11; The American Society of Clinical Oncology.

Madhusudan et al.; "A Phase II Study of Etanercept (Enbrel), a Tumor Necrosis Factor α Inhibitor in Patients with Metastatic Breast Cancer"; Clinical Cancer Research; Oct. 1, 2004; pp. 6528-6534; vol. 10; American Association for Cancer Research.

Marko et al.; "Methodology article, A robust method for the amplification of RNA in the sense orientation"; BMC Genomics, BioMed Central, Open Access; 2005; pp. 1-13; vol. 6, No. 27; Marko et al.; licensee BioMed Central Ltd.

Martincic et al.; "Detection of mutations by automated fluorescence/RNA-based dideoxy fingerprinting (ARddF)"; Oncogene; 1999; pp. 617-621; vol. 18; Stockton Press.

Michell et al.; "Review Article, Biomarkers and Parkinson's disease"; Brain; 2004; pp. 1693-1705; vol. 127, No. 8; Guarantors of Brain.

Miura et al.; "Serum Human Telomerase Reverse Transcriptase Messenger RNA as a Novel Tumor Marker for Hepatocellular Carcinoma"; Clinical Cancer Research, Imaging, Diagnosis, Prognosis; May 1, 2005; pp. 3205-3209; vol. 11, No. 9; American Association for Cancer Research.

Moenner et al.; "Ribonuclease Inhibitor Protein of Human Erythrocytes: Characterization, Loss of Activity in Response to Oxidative Stress, and Association with Heinz Bodies"; Blood Cells, Molecules, and Diseases; Apr. 30, 1998; pp. 149-164; vol. 24, No. 8; Academic Press.

Mrena et al.; "Cyclooxygenase-2 Is an Independent Prognostic Factor in Gastric Cancer and Its Expression Is Regulated by the Messenger RNA Stability Factor HuR"; Clinical Cancer Research, Imaging, Diagnosis, Prognosis; Oct. 15, 2005; pp. 7362-7368; vol. 11, No. 20; American Association for Cancer Research.

Muthukumar, M.D. et al.; "Messenger RNA for FOXP3 in the Urine of Renal-Allograft Recipients"; New England Journal of Medicine; Dec. 1, 2005; pp. 2342-2351; vol. 353, No. 22; Massachusetts Medical Society.

Ng et al.; "Piesence of Filterable and Nonfilterable mRNA in the Plasma of Cancer Patients and Healthy Individuals"; Clinical Chemistry, Cancer Diagnostics: Discovery and Clinical Applications; 2002; pp. 1212-1217; vol. 48, No. 8; American Association for Clinical Chemistry.

Pileur et al.; "Selective inhibitory DNA aptamers of the human RNase H1"; Nucleic Acids Research; 2003; pp. 5776-5788; vol. 31, No. 19; Oxford University Press.

Probst et al.; "Research, Characterization of the ribonuclease activity on the skin surface"; Genetic Vaccines and Therapy, BioMed Central, Open Access; 2006; pp. 1-9; vol. 4, No. 4 ; Probst et al.; licensee BioMed Central Ltd.

Proske et al.; "Aptamers-basic research, drug development, and clinical applications"; Appl Microbiol Biotechnol; 2005; pp. 367-374; vol. 69; Springer-Verlag.

Pullmann, Jr. et al.; "Analysis of Turnover and Translation Regulatory RNA-Binding Protein Expression through Binding to Cognate mRNAs"; Molecular and Cellular Biology; Sep. 2007; pp. 6265-6278; vol. 27, No. 18.

Ranganathan et al.; "Proteomic profiling of cerebrospinal fluid identifies biomarkers for amyotrophic lateral sclerosis"; Journal of Neurochemistry; Dec. 2005; pp. 1461-1471; vol. 95, No. 5.

Rashtchian, Ayoub; Amplification of RNA; PCR Methods and Applications, Manual Supplement; 1994; pp. S83-S91; Cold Springs Harbor Laboratory.

Reddi, K. K.; Holland, James F.; "Elevated serum ribonuclease in patients with pancreatic cancer"; Proc. Natl. Acad. Sci. USA, Biochemistry; Jul. 1976; pp. 2308-2310; vol. 73, No. 7.

Revkin et al.; "Biomarkers in the Prevention and Treatment of Atherosclerosis: Need, Validation, and Future"; Pharmacological Reviews; 2007; pp. 40-53; vol. 59, No. 1; The American Society for Pharmacology and Experimental Therapeutics.

Rudolph et al.; "Identification of RNase 8 as a Novel Human Antimicrobial Protein"; Antimicrobial Agents and Chemotherapy; Sep. 2006; pp. 3194-3196; vol. 50, No. 9; American Society for Microbiology.

Ruiz-Pesini et al.; "An enhanced MITOMAP with a global mtDNA mutational phylogeny"; Nucleic Acids Research; Dec. 18, 2006; pp. D823-D828; vol. 35; The Author(s).

Russo, Nello; Shapiro, Robert; "Potent Inhibition of Mammalian Ribonucleases by 3',5'-Pyrophosphate-linked Nucleotides"; The Journal of Biological Chemistry; May 21, 1999; pp. 14902-14908; vol. 274, No. 21; The American Society for Biochemistry and Molecular Biology, Inc.

Sassan et al.; "Review and Perspective, MicroRNA-implications for cancer"; Virchows Arch; 2008; pp. 1-10; vol. 452; Springer-Verlag.

Silva et al.; "Research Article, Circulating Bmi-1 mRNA as a possible prognostic factor for advanced breast cancer patients"; Breast Cancer Research, Open Access; 2007, pp. 1-9; vol. 9, No. 4; Silva et al.; licensee BioMed Central Ltd.

Smith et al.; "Potent Inhibition of Ribonuclease A by Oligo(vinylsulfonic Acid)*"; The Journal of Biological Chemistry; Jun. 6, 2003; pp. 20934-20938; vol. 278, No. 23; The American Society for Biochemistry and Molecular Biology, Inc.

Spencer et al.; "Toward the Design of Ribonuclease (RNase) Inhibitors: Ion Effects on the Thermodynamics of Binding of 2'-CMP to RNase A"; The Journal of Pharmacology and Experimental Therapeutics; 2002; pp. 925-929; vol. 301, No. 3; The American Society for Pharmacology and Experimental Therapeutics.

Spurgeon et al.; "High Throughput Gene Expression Measurement with Real Time PCR in a Microfluidic Dynamic Array"; Feb. 2008; pp. 1-7; vol. 3, Issue 2.

Tsui et al.; "Stability of Endogenous and Added RNA in Blood Specimens, Serum, and Plasma"; Clinical Chemistry, Molecular Diagnostics and Genetics; 2002; pp. 1647-1653; vol. 48, No. 10.

Uchida et al.; "Cancer Therapy: Clinical, Intratumoral COX-2 Gene Expression Is a Predictive Factor for Colorectal Cancer Response to Fluoropyrimidine-Based Chemotherapy"; Clinical Cancer Research; May 1, 2005; pp. 3363-3368; vol. 11, No. 9; American Association for Cancer Research.

Wang et al.; "Inhibition of B16 melanoma growth in vivo by retroviral vector-mediated human ribonuclease inhibitor"; Angiogenesis; 2005; pp. 73-81; vol. 8.

Wiel et al.; "Review, Breast Cancer Metastasis to the Central Nervous System"; American Journal of Pathology; Oct. 2005; pp. 913-920; vol. 167, No. 4; American Society for Investigative Pathology.

Yakovlev et al.; "Reviews, Ribonuclease Inhibitors"; Molecular Biology; 2006; pp. 867-874; vol. 40, No. 6; Pleiades Publishing, Inc.

\* cited by examiner

FIG. 1
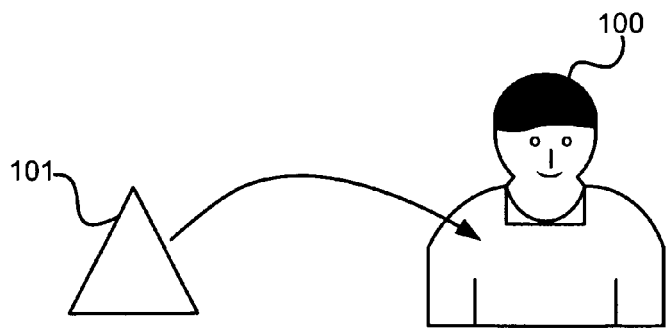
FIG. 1A
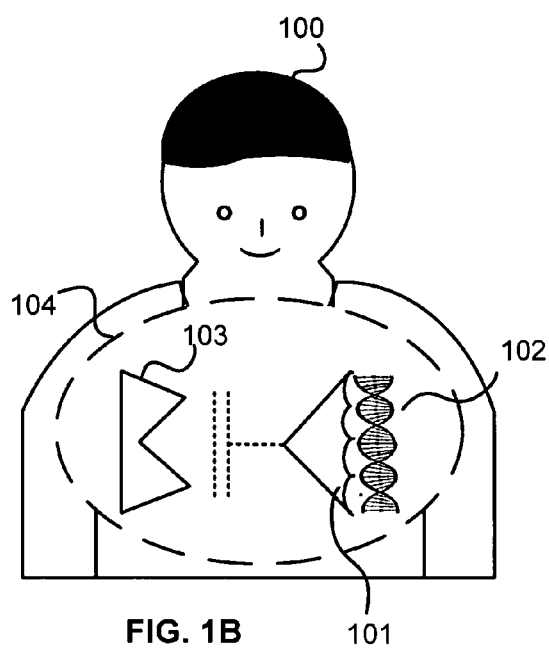
FIG. 1B
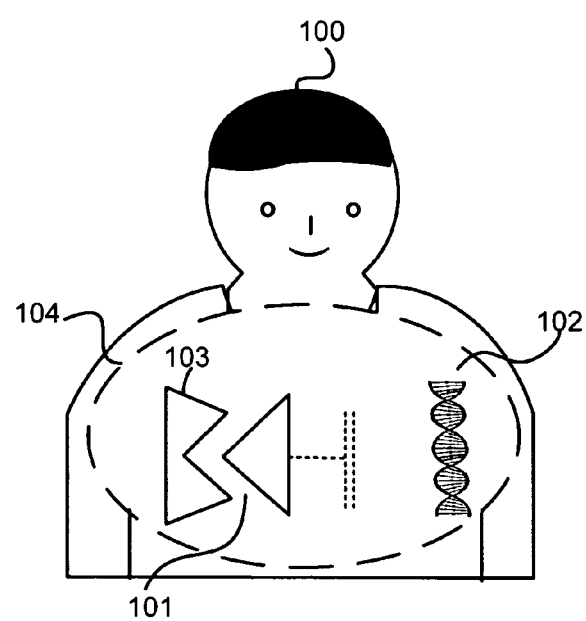
FIG. 1C

FIG. 2
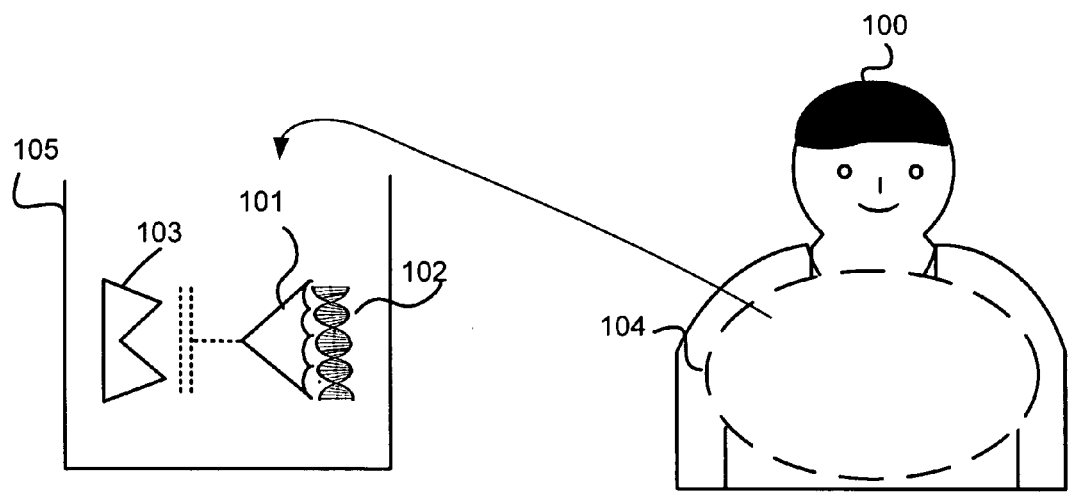
FIG. 2A
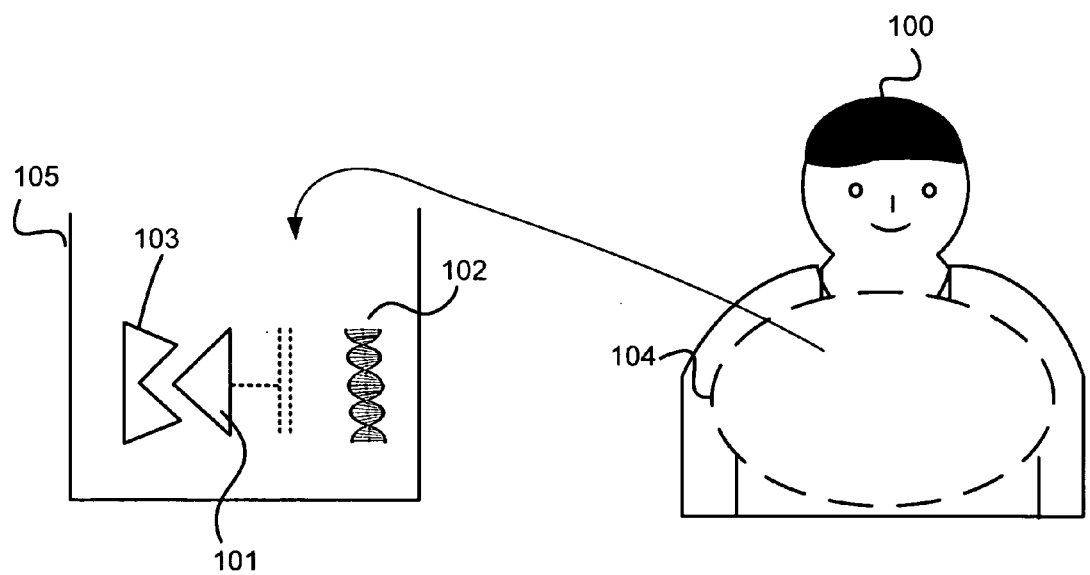
FIG. 2B

FIG. 3
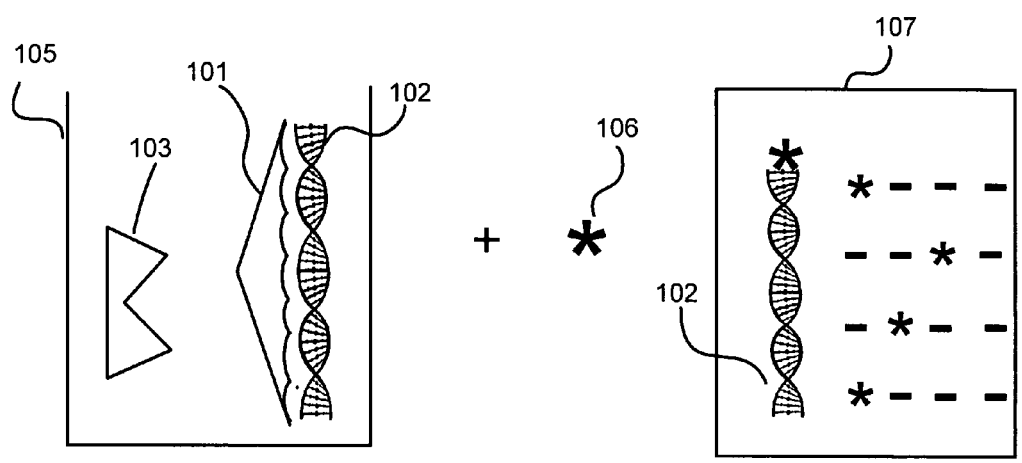
FIG. 3A
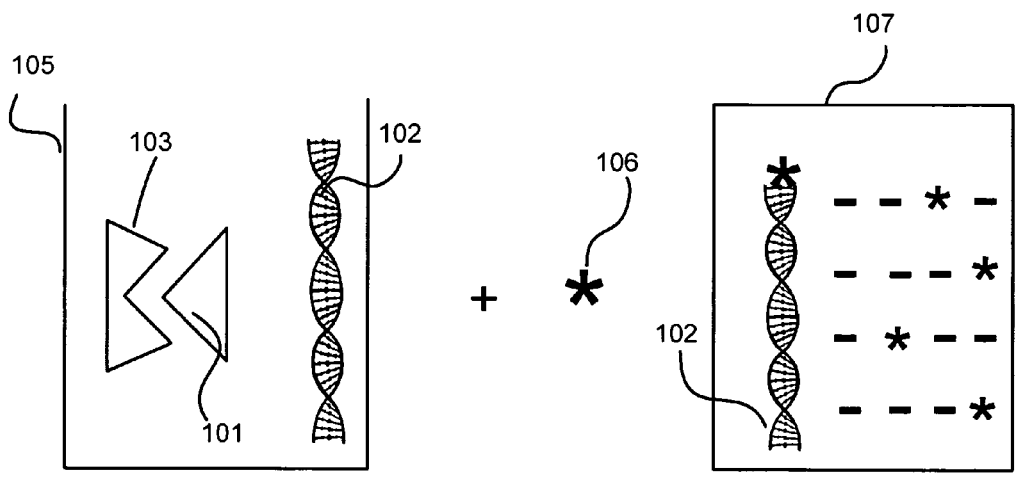
FIG. 3B

FIG. 5A

| 5A | 5B | 5C |

Key To FIG. 5

500 → 401

─Ⓐ administer at least one compound to an animal wherein the at least one compound is configured to prevent the cleavage of at least one tissue RNA by a ribonuclease

─Ⓑ the at least one compound is a ribonuclease binding molecule  501

─Ⓒ

| the ribonuclease binding molecule is configured to prevent transport of the ribonuclease binding molecule across a cell membrane; e.g., the ribonuclease binding molecule is bound to a bead, or joined to a hydrophilic moiety; | the ribonuclease binding molecule has a molecular weight of at least about 600 daltons | the ribonuclease binding molecule is a polypeptide inhibitor of ribonuclease, (e.g., RNasin or human placental inhibitor, an antibody to ribonuclease), or an aptamer to ribonuclease |

502   503   504

─Ⓓ
─Ⓔ
─Ⓕ collect a sample of at least a portion of blood or tissue containing the at least one tissue RNA from the animal

402

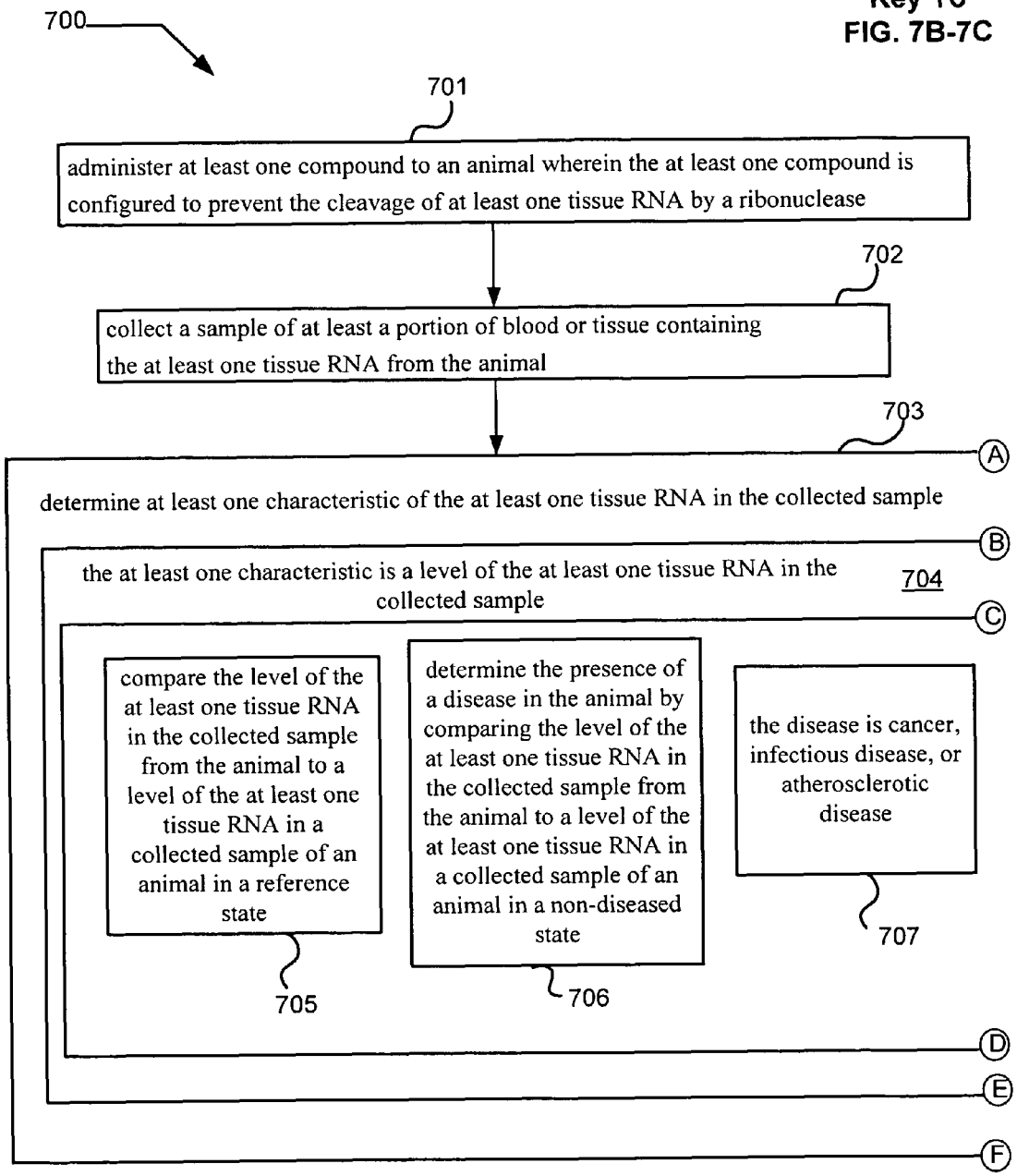

| determining at least one characteristic of at least one tissue RNA in a biological sample from an animal, the animal having been administered at least one compound configured to prevent the cleavage of the at least one tissue RNA by a ribonuclease |
|---|

METHODS FOR COLLECTING AND DETECTING OLIGONUCLEOTIDES

CROSS-REFERENCE TO RELATED APPLICATIONS

The present application is related to U.S. patent application Ser. No. 12/157,984, entitled METHODS, COMPOSITIONS, AND KITS FOR COLLECTING AND DETECTING OLIGONUCLEOTIDES, naming Paul G. Allen, Edward S. Boyden, Roderick A. Hyde, Muriel Y. Ishikawa, Stephen L. Malaska, Dennis J. Rivet, Leif T. Stordal, Lowell L. Wood, Jr. as inventors, filed 12, Jun. 2008.

SUMMARY

The method described herein comprises accurately sampling a RNA from a tissue of an animal and analyzing RNA in the tissue of the animal as an indicator of physiological state, infectious disease, neoplastic disease, autoimmune disease, inflammatory disease, cardiovascular disease, or neurological disease in the animal. Described herein is a method comprising administering at least one compound to an animal wherein the at least one compound is configured to prevent the cleavage of at least one tissue RNA by a ribonuclease. The method further includes collecting a sample of at least a portion of tissue from the animal. The method further includes determining at least one characteristic of the at least one tissue RNA in the collected sample from the animal. The at least one tissue RNA can be derived, for example, from blood, cells, organ tissue, or cerebral spinal fluid.

The method described herein includes administering to an animal at least one compound which is a RNA stabilizing agent configured to prevent the cleavage of at least one tissue RNA by a ribonuclease. The RNA stabilizing agent includes, but is not limited to, a ribonuclease binding molecule or a compound configured to bind or hybridize to the at least one tissue RNA. The method described herein includes administering at least one compound including a ribonuclease-binding molecule. The method described herein includes administering at least one compound including a RNA-binding molecule. In one aspect, the administering step occurs within a defined time before the collecting step. In a further aspect, the at least one compound is bifunctional and includes (1) an RNA stabilizing agent configured to prevent the cleavage of at least one tissue RNA by a ribonuclease and (2) a ribonuclease-binding molecule.

The method described herein includes administering at least one first compound to an animal wherein the at least one first compound is a ribonuclease binding molecule; and administering at least one second compound to the animal wherein the at least one second compound is configured to bind to at least one tissue RNA. The method can further include collecting at least a portion of a blood or tissue sample from the animal. The method can further include determining at least one characteristic of the at least one tissue RNA in the collected tissue sample.

In alternative aspects, the at least one compound configured to bind to the at least one tissue RNA can be an oligonucleotide molecule having a sequence substantially complementary to the nucleotide sequence of the at least one tissue RNA. The at least one compound can be an oligonucleotide molecule having a sequence substantially complementary to at least a portion of the at least one tissue RNA. The at least one compound can be an oligonucleotide molecule having a sequence substantially complementary to a 5' end or 3' end sequence of the at least one tissue RNA. The at least one compound can be an oligonucleotide molecule having a sequence substantially complementary to a nuclease recognition sequence of the at least one tissue RNA. The at least one compound can include, but is not limited to, a small molecule, a RNA, a DNA, a PNA, or an aptamer. The at least one compound configured to bind to the at least one tissue RNA refers to a compound which can bind to or hybridize to the at least one tissue RNA, e.g., a nucleic acid, RNA, DNA, PNA, or analog thereof, or a polypeptide, aptamer, or small molecule having a chemical binding affinity to the at least one tissue RNA, e.g., ionic bond, hydrogen bonding, permanent dipole interaction, van der Waals force or covalent bond.

The at least one tissue RNA can be from blood, cells, organ tissue, or cerebral spinal fluid. The at least one tissue RNA can include, but is not limited to, mRNA. transfer RNA or ribosomal RNA microRNA, mitochondrial RNA or pathogen RNA. The pathogen RNA can be from bacteria, virus, or parasite.

In the method as described herein, the at least one characteristic can be a level of the at least one tissue RNA in the collected sample. The method can further comprise comparing the level of the at least one tissue RNA in the collected sample from the animal to a level of the at least one tissue RNA in a collected sample of an animal in a reference state. The method can further comprise determining the presence of a disease in the animal by comparing the level of the at least one tissue RNA in the collected sample from the animal to a level of the at least one tissue RNA in a collected sample of an animal in a non-diseased state. The disease can include, but is not limited to, infectious disease, neoplastic disease, autoimmune disease, inflammatory disease, cardiovascular disease, atherosclerotic disease, or neurological disease.

In the method as described herein, the at least one characteristic is an identity of the at least one tissue RNA, or the at least one characteristic is an identity of the at least one tissue RNA associated with a disease state. In the method as described herein, the at least one characteristic is a relative level of at least two different RNAs, or the at least one characteristic is a relative level of at least two different RNAs associated with a disease state. In the method as described herein, the at least one characteristic is a relative level of the at least one tissue RNA measured at two or more time points. In the method as described herein, the at least one characteristic is a relative level of at least two different RNAs measured in two different tissues in the animal, or the at least one characteristic is a relative level of at least two different RNAs measured at two different locations in the animal. In one aspect, the animal is human.

The ribonuclease binding molecule can be configured to prevent transport of the ribonuclease binding molecule across a cell membrane. The ribonuclease binding molecule can be bound to a bead. The ribonuclease binding molecule can be joined to a hydrophilic moiety. The ribonuclease binding molecule can have a molecular weight of at least about 600 daltons. The ribonuclease binding molecule can be a polypeptide inhibitor of ribonuclease, a small molecule inhibitor, an antibody to ribonuclease, or an aptamer to ribonuclease. The ribonuclease binding molecule can be, for example, RNasin. The ribonuclease binding molecule can be, for example, a human placental inhibitor. In one aspect, the at least one tissue RNA is released from a cell that is undergoing or has undergone apoptosis.

The method described herein comprises determining at least one characteristic of at least one tissue RNA in a biological sample from an animal, the sample collected from the animal having been administered at least one compound configured to prevent the cleavage of the at least one tissue RNA by a ribonuclease.

A method of sampling at least one tissue RNA from an animal is provided which comprises collecting a sample of at least a portion of fluid or tissue containing the at least one tissue RNA from the animal, the animal having been administered at least one compound configured to prevent the cleavage of the at least one tissue RNA by a ribonuclease. The method can further comprise determining at least one characteristic of the at least one tissue RNA in the collected sample. The at least one characteristic can be a level of the at least one tissue RNA in the collected sample. The method can further comprise determining the presence of a disease in the animal by comparing the level of the at least one tissue RNA in the collected sample from the animal to a level of the at least one tissue RNA in a collected sample of an animal in a non-diseased state. The at least one characteristic can include, but is not limited to, an identity of the at least one tissue RNA associated with a disease state, a relative level of at least two different RNAs associated with a disease state, or a relative level of the at least one tissue RNA measured at two or more time points. The fluid or tissue includes, but is not limited to, whole blood, blood plasma, serum, urine, effusions, ascites, saliva, cerebrospinal fluid, cervical secretions, endometrial secretions, semen, gastrointestinal secretions, bronchial secretions, or breast fluid, or organ tissue.

The at least one tissue RNA can be from blood, cells, organ tissue, or cerebral spinal fluid. The organ tissue refers to a structure which is a specific part of an individual organism where a certain function of the individual organism is locally performed and which is morphologically independent. Generally in animals, organs are made of several tissues in specific spatial arrangement and tissue is made of a number of cells. Examples of such organs include, but are not limited to, skin, blood vessel, cornea, kidney, heart, liver, umbilical cord, intestine, nerve, lung, placenta, pancreas, brain, joint, bone, cartilage, peripheral limbs, retina. Examples of such organs include, but are not limited to, organs of the skin system, the parenchyma pancreas system, the pancreatic duct system, the hepatic system, the blood system, the myocardial system, the skeletal muscle system, the osteoblast system, the skeletal myoblast system, the nervous system, the blood vessel endothelial system, the pigment system, the smooth muscle system, the fat system, the bone system, the cartilage system.

A pharmaceutical composition is described which comprises a first compound and a second compound wherein the first compound is a ribonuclease binding molecule and the second compound is configured to bind to at least one tissue RNA The at least one tissue RNA can include, but is not limited to, RNA from whole blood, blood plasma, serum, urine, effusions, ascites, saliva, cerebrospinal fluid, cervical secretions, endometrial secretions, semen, gastrointestinal secretions, bronchial secretions, or breast fluid, or organ tissue. The ribonuclease binding molecule can be configured to prevent transport of the ribonuclease binding molecule across a cell membrane. The ribonuclease binding molecule can be bound to a bead. The ribonuclease binding molecule can be joined to a hydrophilic moiety. The ribonuclease binding molecule can have a molecular weight of at least about 600 daltons. The ribonuclease binding molecule can include, but is not limited to, a polypeptide inhibitor of ribonuclease, an antibody to ribonuclease, an aptamer to ribonuclease, a human placental RNase inhibitor e.g., RNasin®. The second compound can be an oligonucleotide molecule having a sequence substantially complementary to the nucleotide sequence of the at least one tissue RNA. The at least one compound can include, but is not limited to, an oligonucleotide molecule having a sequence substantially complementary to at least a portion of the at least one tissue RNA, an oligonucleotide molecule having a sequence substantially complementary to a 5' end or 3' end sequence of the at least one tissue RNA, or an oligonucleotide molecule having a sequence substantially complementary to a nuclease recognition sequence of the at least one tissue RNA. Further, the second compound can include, but is not limited to, a small molecule, a RNA, a DNA, a PNA, or an aptamer. The at least one tissue RNA can include, but is not limited to, mRNA, transfer RNA, ribosomal RNA, microRNA, mitochondrial RNA, pathogen RNA wherein the pathogen RNA is from bacteria, virus, or parasite.

A kit is described which comprises a pharmaceutical composition comprising a first compound and a second compound wherein the first compound is a ribonuclease binding molecule and the second compound is configured to bind to at least one tissue RNA, the pharmaceutical composition capable of being administered to an animal. The kit can further comprise a container to collect a blood sample from the animal to determine at least one characteristic of at least one tissue RNA in the blood sample. The at least one characteristic can be a level of the at least one tissue RNA in the collected sample. The kit can further comprise an assay to determine presence of a disease in the animal by comparing the level of the at least one tissue RNA in the collected sample from the animal to a level of the at least one tissue RNA in a collected sample of an animal in a non-diseased state. The at least one characteristic can be an identity of the at least one tissue RNA associated with a disease state. The disease state can include, but is not limited to, infectious disease, neoplastic disease, autoimmune disease, inflammatory disease, cardiovascular disease, atherosclerotic disease, or neurological disease. The at least one characteristic can include, but is not limited to, a relative level of at least two different RNAs associated with a disease state, or a relative level of the at least one tissue RNA measured at two or more time points.

BRIEF DESCRIPTION OF THE FIGURES

FIGS. 1A, 1B, and 1C depict some aspects of a method that may serve as an illustrative environment for subject matter technologies.

FIGS. 2A and 2B depict some aspects of a method that may serve as an illustrative environment for subject matter technologies.

FIGS. 3A and 3B depict some aspects of a method that may serve as an illustrative environment for subject matter technologies.

FIGS. 5A, 5B, and 5C illustrate exemplary aspects of a method such as those depicted in FIGS. 1, 2, and 3.

FIGS. 7A, 7B, and 7C illustrate exemplary aspects of a method such as those depicted in FIGS. 1, 2, and 3.

DETAILED DESCRIPTION

Figure 4:
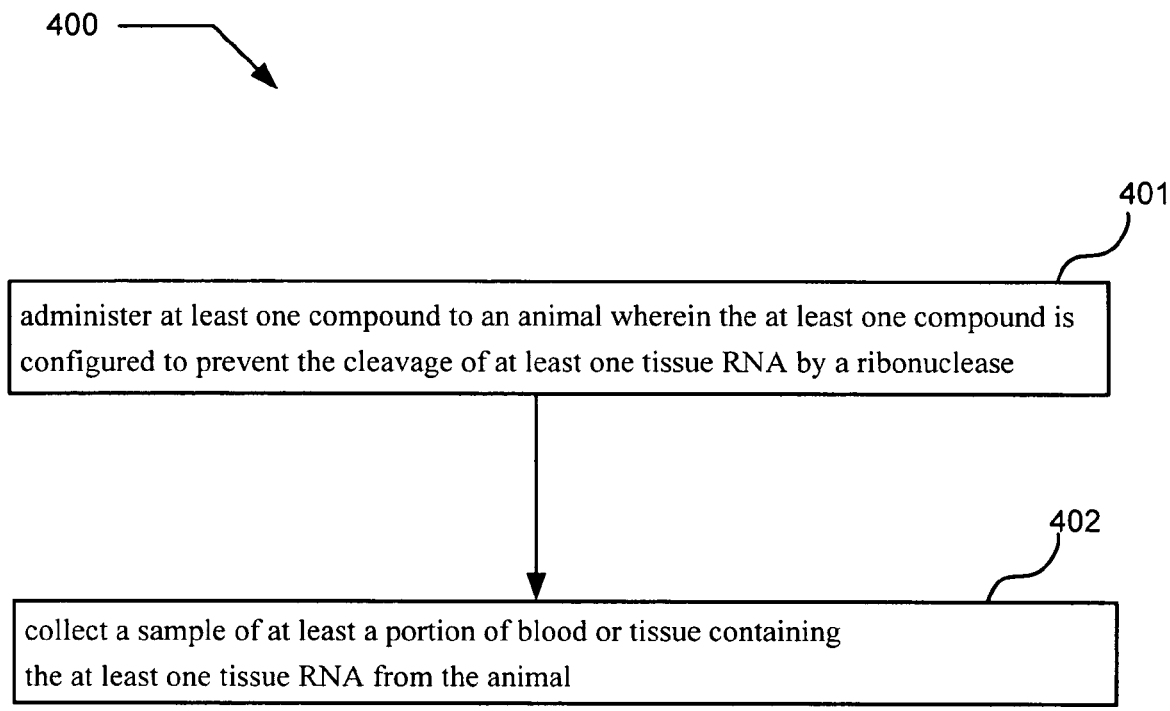
FIG. 4 illustrates exemplary aspects of a method such as those depicted in FIGS. 1, 2 and 3.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The present application uses formal outline headings for clarity of presentation. However, it is to be understood that the outline headings are for presentation purposes, and that different types of subject matter may be discussed throughout the application (e.g., method(s) may be described under composition heading(s) and/or kit headings; and/or descriptions of single topics may span two or more topic headings). Hence, the use of the formal outline headings is not intended to be in any way limiting.

The method described herein comprises sampling a RNA from a biological tissue of an animal and analyzing the RNA as an indicator of, for example, a physiological state, infectious disease, neoplastic disease, autoimmune disease, inflammatory disease, cardiovascular disease, atherosclerotic disease, or neurological disease in the animal. Described herein is a method comprising administering at least one compound to an animal wherein the at least one compound is configured to prevent the cleavage of at least one tissue RNA by a ribonuclease. The method further includes collecting a sample of at least a portion of biological tissue from the animal. The method further includes determining at least one characteristic of the at least one tissue RNA in the collected sample from the animal. RNA can be collected from any biological tissue of an animal. As used herein, the terms "biological tissue" and "tissue" are used interchangeably and include, but are not limited to, blood, body fluids, organ tissue, nerve tissue, muscle tissue, epithelial tissue, and connective tissue.

An animal includes, for example, a human, a non-human primate, as well as experimental animals such as rabbits, rats, mice, and other animals. Animals include all vertebrates, e.g., mammals and non-mammals, such as sheep, dogs, cows, chickens, amphibians, and reptiles. An animal further includes, for example, a pet, experimental animals, livestock, zoo animals, or animals in the wild.

The method described herein includes administering to an animal at least one compound which is a RNA stabilizing agent configured to prevent the cleavage of at least one tissue RNA by a ribonuclease. The RNA stabilizing agent includes, but is not limited to, a ribonuclease binding molecule or a compound configured to bind to at least one tissue RNA.

The methods described herein apply to a dynamic system which can be applicable to real-time diagnosis of physiological or disease states, for example, in critical care settings. Generally, tissue RNAs have short half-lives and have less complexity in tissue than proteins for current detection technologies. By determining at least one characteristic of the at least one tissue RNA in the collected sample from the animal, one can determine, for example, a signature of aberrant state(s) in the animal. In one aspect, one can measure a characteristic gradient in the body as an indicator of location and/or flow of aberrant RNA sources. For example one can measure spatial gradients, and/or temporal gradients as an indicator of location and/or flow of aberrant RNA sources. Such measurements can indicate cellular leakage, apoptosis, infection and/or inflammatory cell aberrant states, e.g., associated with infectious disease, neoplastic disease, autoimmune disease, inflammatory disease, cardiovascular disease, atherosclerotic disease, or neurological disease. The method described herein can be used to collect samples over various time points before and during treatment of disease to examine progression or recurrence of a medical event, such as cancer progression, regression or recurrence.

The method described herein can further comprise determining characteristics of one or a selected group of RNAs as molecular markers or indicators of disease. The methods can be used to monitor tissues including but not limited to, CSF, such as from CSF shunts, tissue biopsy, or blood, which can be obtained during a medical procedure.

In one aspect, the at least one compound is configured to bind to at least one tissue RNA in the animal. The method can provide injecting a tagged RNA-binding molecule into the animal that would hybridize to a target RNA. Binding of the tagged molecule to the target RNA would induce a detectable change. The tag may be any suitable molecule for detection. For example, a tag may include, but is not limited to, a fluorescing molecule, a quantum dot, or a radioisotope. A characteristic measurement may involve detecting a quenching or change in the fluorescent signal after hybridization. Methods for measuring levels or amounts of RNA from a tissue in the animal include the use of an electrically active surface with RNA attached. Upon hybridization a change in electrical actuation occurs. Other assays include RNA binding to a cofactor to induce a color change or other visible indicator. The methods described herein are applicable to a dynamic system which can be applicable for a real-time diagnostic of physiological or disease states. The multivalent assay system can measure multiple tissue RNAs in a tissue sample from the animal in a temporal or spatial gradient.

Cleavage of tissue RNA by a ribonuclease may be prevented or modulated either by at least one compound configured to bind the ribonuclease, or at least one compound configured to bind to the tissue RNA in such a way to sterically hinder ribonuclease activity, or by both. Ribonuclease binding compounds include, for example, a small molecule, a polypeptide, antibody, nucleic acid, RNA, DNA, PNA, or an aptamer. The compound configured to bind to the at least one tissue RNA includes, for example, a small molecule, a nucleic acid, RNA, DNA, PNA, or an aptamer.

With reference to the figures, and with reference now to FIGS. 1, 2, and 3, depicted is one aspect of a system that may serve as an illustrative environment of and/or for subject matter technologies, for example, a method including administering at least one compound to an animal wherein the at least one compound is configured to prevent the cleavage of at least one tissue RNA by a ribonuclease, and collecting a sample of at least a portion of blood or tissue containing the at least one tissue RNA from the animal. Accordingly, the present application first describes certain specific exemplary methods of FIGS. 1, 2, and 3; thereafter, the present application illustrates certain specific exemplary methods. Those having skill in the art will appreciate that the specific methods described herein are intended as merely illustrative of their more general counterparts.

Continuing to refer to FIG. 1, depicted is a partial view of a method that may serve as an illustrative environment of and/or for subject matter technologies. In FIGS. 1A and 1B, a method includes administering at least one compound 101 to an animal 100 in a tissue 104 of the animal. In FIGS. 1B and 1C, the at least one compound 101 is configured to prevent the cleavage of at least one tissue RNA 102 by a ribonuclease 103. In FIG. 1B, the at least one compound 101 is configured to bind to the at least one tissue RNA 102. In FIG. 1C, the at least one compound 101 is a ribonuclease binding molecule 101 which is configured to prevent the cleavage of at least one tissue RNA 102 by a ribonuclease 103.

FIG. 2 depicts some exemplary aspects of a method as that described in FIG. 1. In FIGS. 2A and 2B, the method further includes collecting a sample 105 of at least a portion of blood or tissue 104 containing the at least one tissue RNA 102 from the animal 100. In FIG. 2A, the at least one compound 101 is configured to bind to the at least one tissue RNA 102 and is configured to prevent the cleavage of the at least one RNA. In FIG. 2B, the at least one compound 101 is a ribonuclease binding molecule 101 which is configured to prevent the cleavage of at least one tissue RNA 102 by a ribonuclease 103.

FIG. 3 depicts some exemplary aspects of a method as that described in FIGS. 1 and 2. In FIGS. 3A and 3B, the method further includes determining at least one characteristic of the at least one tissue RNA in the collected sample 105. For example, the at least one tissue RNA 102 can be detected with a labeled probe 106, and characterized on an array 107 to determine the identity of the at least one tissue RNA 102.

FIG. 4 illustrates exemplary aspects of a method such as those depicted in FIGS. 1, 2 and 3. An exemplary embodiment includes a method 400 comprising administering at least one compound to an animal wherein the at least one compound is configured to prevent the cleavage of at least one tissue RNA by a ribonuclease 401 and collecting a sample of at least a portion of blood or tissue containing the at least one tissue RNA from the animal 402.

Figure 5B:
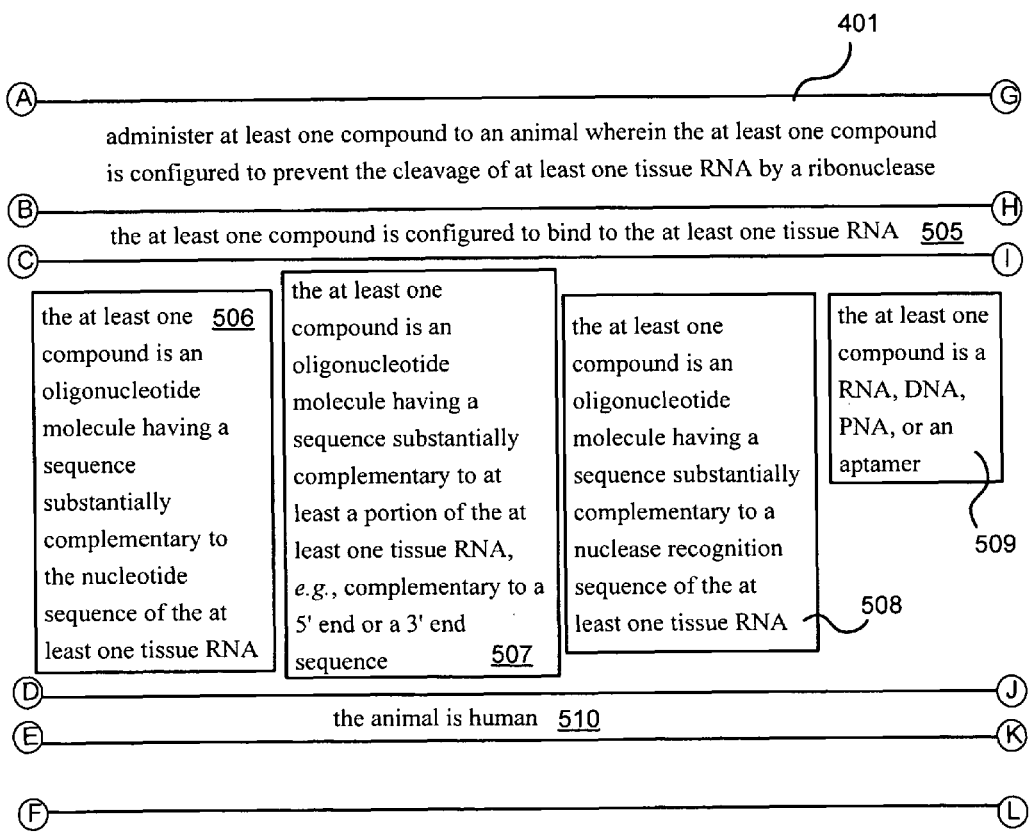
Figure 5C:
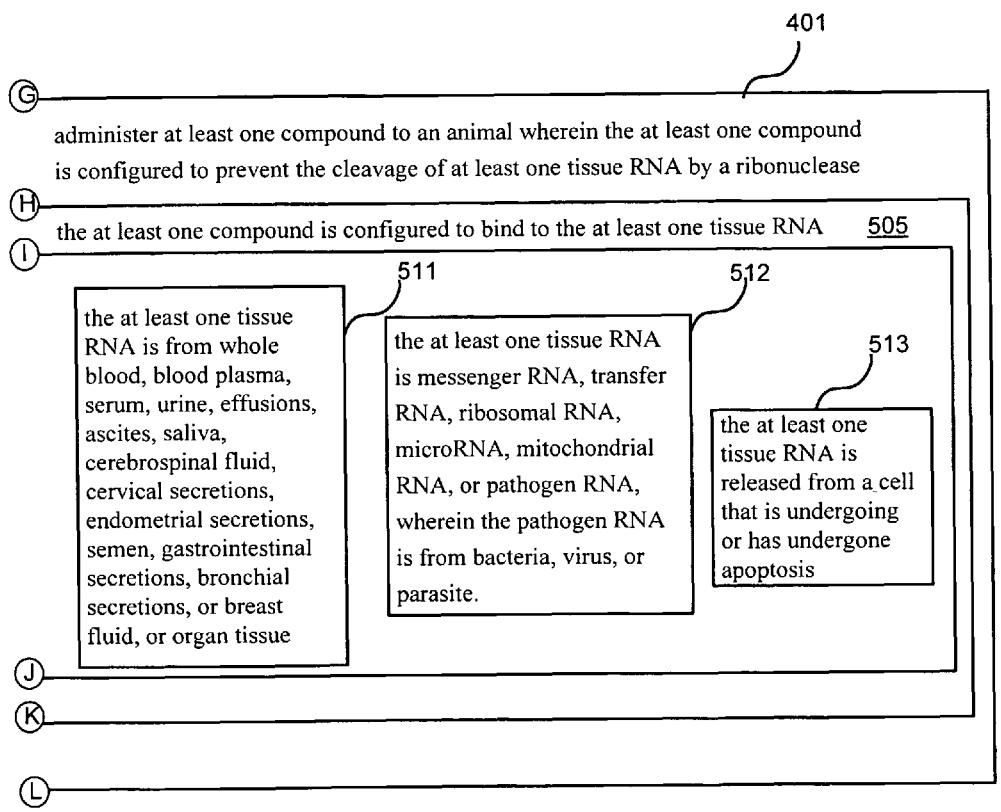

FIG. 5 illustrates exemplary aspects of a method such as those depicted in FIGS. 1, 2, and 3. FIG. 5A illustrates an exemplary method 500 comprising administering at least one compound to an animal wherein the at least one compound is configured to prevent the cleavage of at least one tissue RNA by a ribonuclease 401 and collecting a sample of at least a portion of blood or tissue containing the at least one tissue RNA from the animal, 402, wherein the at least one compound is a ribonuclease binding molecule 501, and further exemplary aspects of the ribonuclease binding molecule 502, 503, 504. FIG. 5B illustrates the exemplary method, as above, wherein the at least one compound is configured to bind to the at least one tissue RNA 505 and further exemplary aspects of the at least one compound is configured to bind to the at least one tissue RNA 506, 507, 508, 509. FIG. 5C illustrates the exemplary method, as above, wherein the at least one compound is configured to bind to the at least one tissue RNA 505 and further exemplary aspects of the at least one tissue RNA 511, 512, 513.

Figure 6:
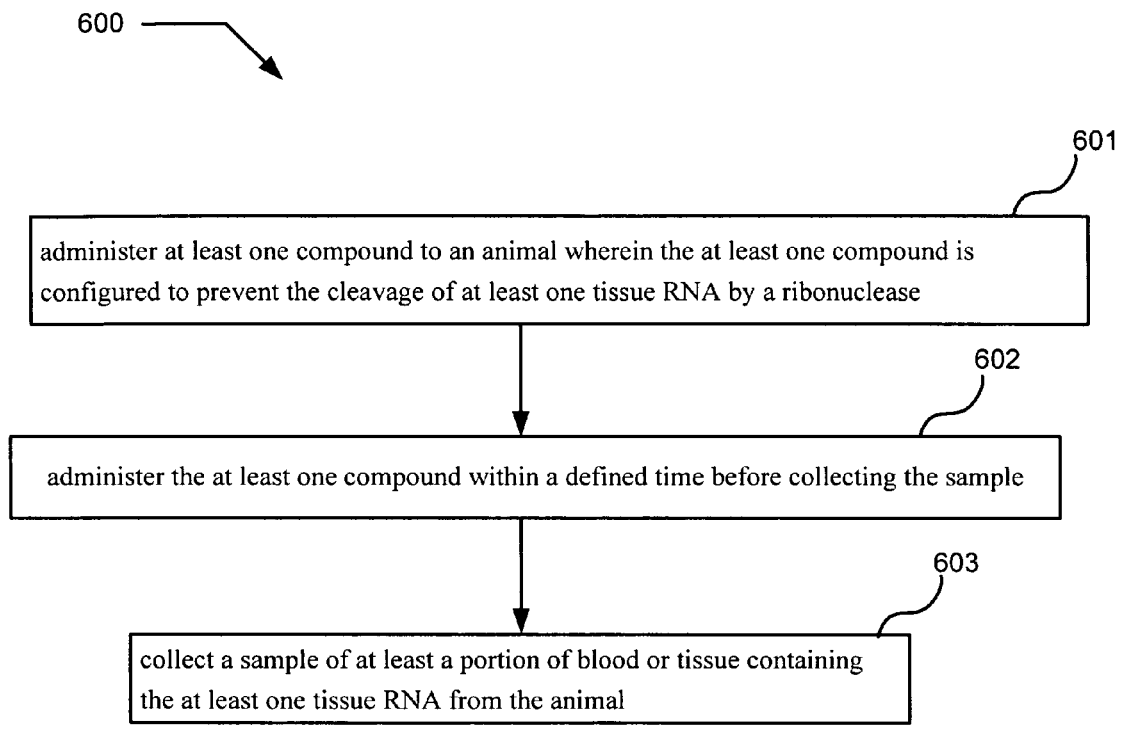
FIG. 6 illustrates exemplary aspects of a method such as those depicted in FIGS. 1, 2, and 3.

FIG. 6 illustrates exemplary aspects of a method such as those depicted in FIGS. 1, 2, and 3. FIG. 6 illustrates an exemplary method 600 comprising administering at least one compound to an animal wherein the at least one compound is configured to prevent the cleavage of at least one tissue RNA by a ribonuclease 601, administering at least one compound occurs within a defined time before the collecting of the sample 602, and collecting a sample of at least a portion of blood or tissue containing the at least one tissue RNA from the animal, 603.

Figure 7A:
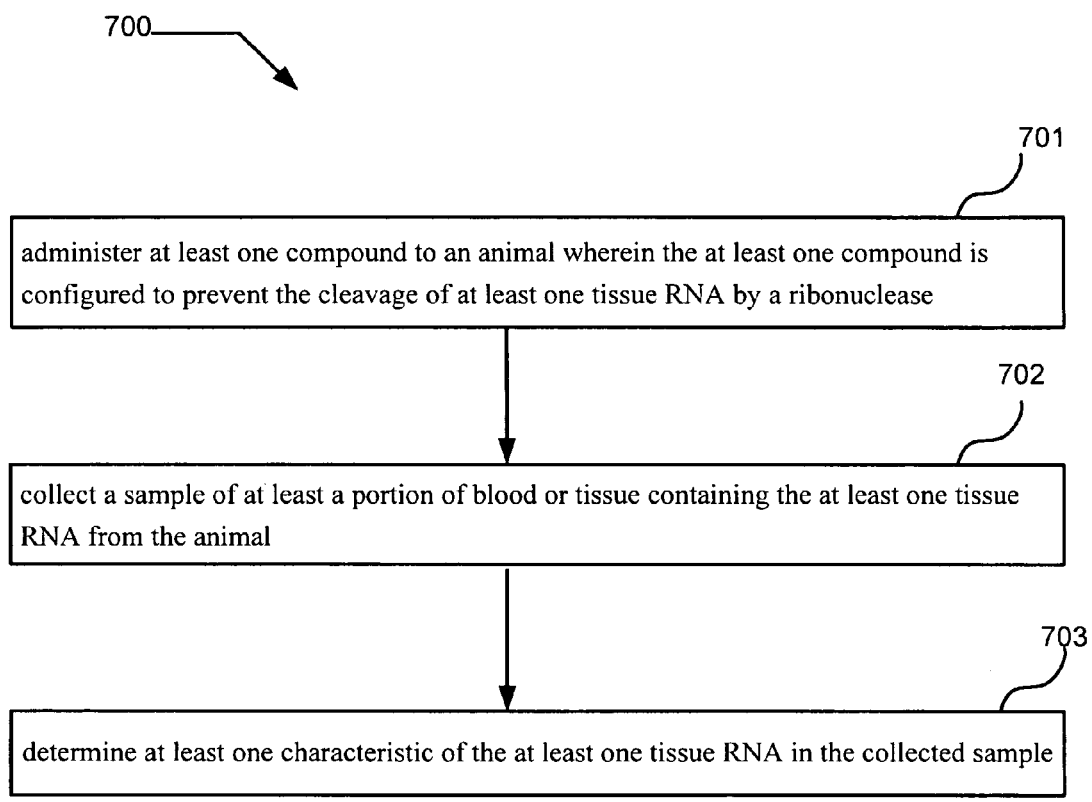
Figure 7C:
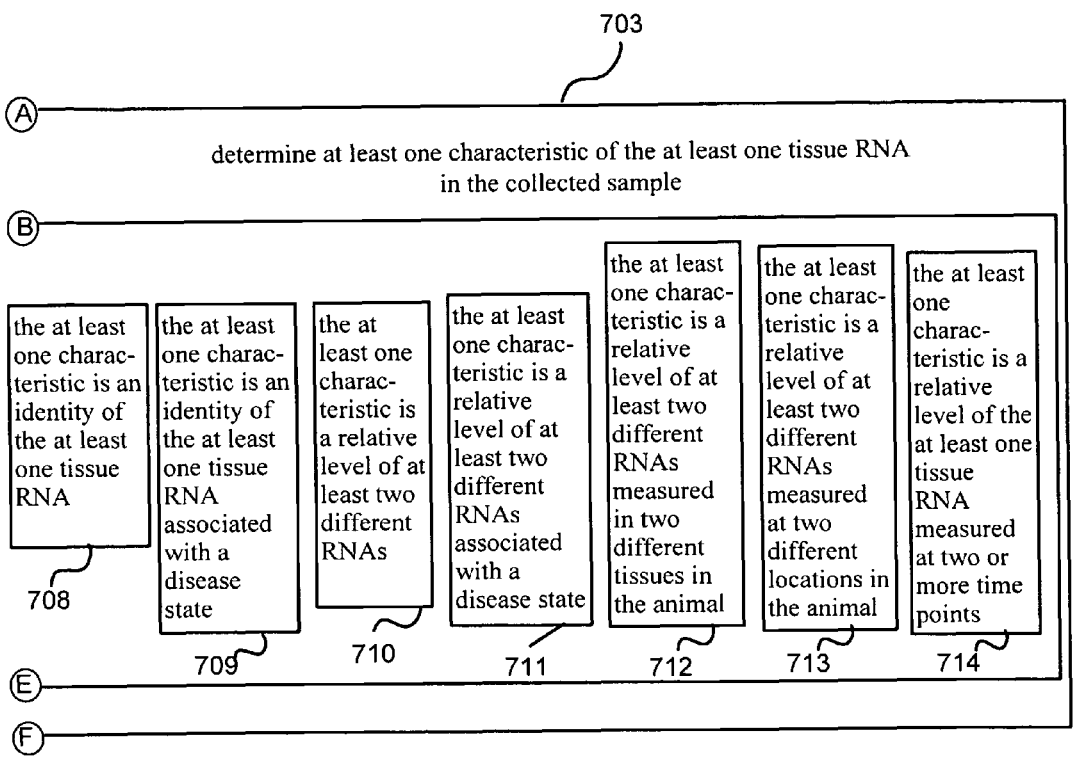

FIG. 7 illustrates exemplary aspects of a method such as those depicted in FIGS. 1, 2, and 3. FIG. 7A illustrates an exemplary method 700 comprising administering at least one compound to an animal wherein the at least one compound is configured to prevent the cleavage of at least one tissue RNA by a ribonuclease 701, collecting a sample of at least a portion of blood or tissue containing the at least one tissue RNA from the animal, 702, and determining at least one characteristic of the at least one tissue RNA in the collected sample 703. FIG. 7B illustrates the exemplary method, as above, wherein the at least one characteristic is a level of the at least one tissue RNA in the collected sample 704, and exemplary aspects of the at least one characteristic being a level of the at least one tissue RNA in the collected sample 705, 706, 707. FIG. 7C illustrates the exemplary method, as above, wherein the determining at least one characteristic of the at least one tissue RNA in the collected sample 703 provides embodiments of the at least one characteristic of the at least one tissue RNA in the collected sample 708, 709, 710, 711, 712, 713, 714.

Figure 8:
FIG. 8 illustrates exemplary aspects of a method such as those depicted in FIGS. 1, 2, and 3.
Figure 8:
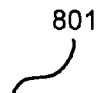

FIG. 8 illustrates exemplary aspects of a method such as those depicted in FIGS. 1, 2, and 3. FIG. 8 illustrates an exemplary method 800 comprising determining at least one characteristic of at least one tissue RNA in a biological sample from an animal, the animal having been administered at least one compound configured to prevent the cleavage of the at least one tissue RNA by a ribonuclease 801.

Figure 9:
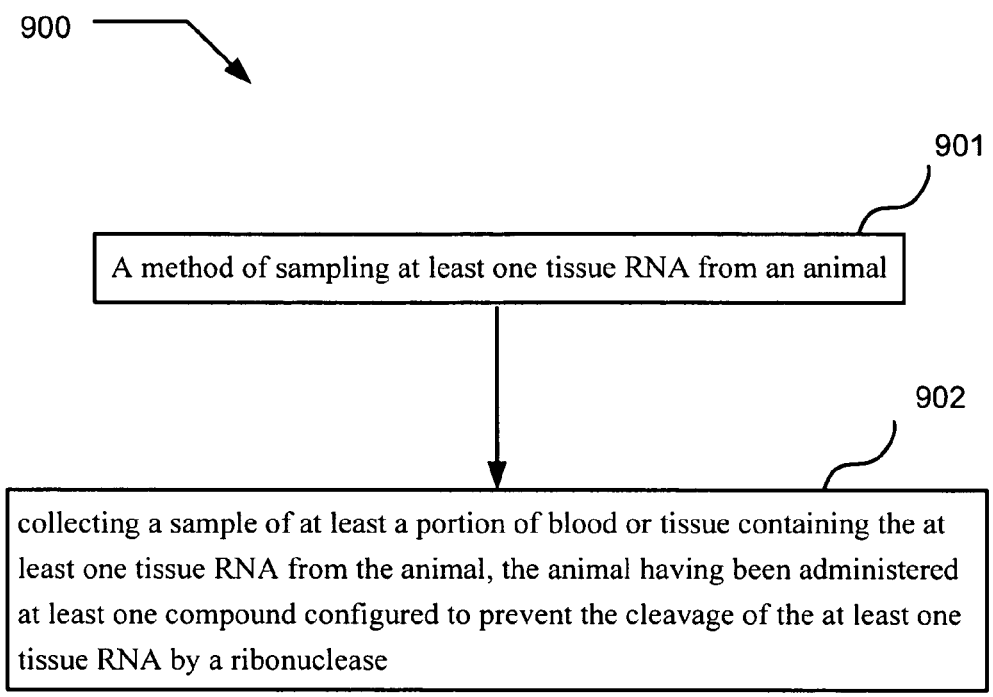
FIG. 9 illustrates exemplary aspects of a method such as those depicted in FIGS. 1, 2, and 3.

FIG. 9 illustrates exemplary aspects of a method such as those depicted in FIGS. 1, 2, and 3. FIG. 9 illustrates an exemplary method 900 of sampling at least one tissue RNA from an animal 901 comprising collecting a sample of at least a portion of blood or tissue containing the at least one tissue RNA from the animal, the animal having been administered at least one compound configured to prevent the cleavage of the at least one tissue RNA by a ribonuclease 902.

An intact antibody comprises at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxyl-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) through cellular receptors such as Fc receptors (e.g., FcγRI, FcγRIIa, FcγRIIb, FcγRIII, and FcR) and the first component (C1q) of the classical complement system. The term antibody includes antigen-binding portions of an intact antibody that retain capacity to bind the antigen. Examples of antigen binding portions include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., *Nature* 341: 544-546, 1989, which is incorporated herein by reference), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); See, e.g., Bird et al., *Science* 242: 423-426, 1988; and Huston et al., *Proc. Natl. Acad. Sci. U.S.A.* 85: 5879-5883, 1988, which are incorporated herein by reference). Such single chain antibodies are included by reference in the term "antibody." Fragments can be prepared by recombinant techniques or enzymatic or chemical cleavage of intact antibodies.

"Human sequence antibody" includes antibodies having variable and constant regions (if present) derived from human immunoglobulin sequences. The human sequence antibodies described herein can include amino acid residues not encoded by human germline immunoglobulin sequences (e.g., mutations introduced by random or site-specific mutagenesis in vitro or by somatic mutation in vivo).

"Humanized antibody" includes antibodies in which entire CDR sequences sufficient to confer antigen specificity and derived from the germline of another mammalian species, such as a mouse, have been grafted onto human framework sequences.

"Monoclonal antibody" or "monoclonal antibody composition" refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions (if present) derived from human germline immunoglobulin sequences. In one embodiment, the human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell. "Diclonal antibody" refers to a preparation of at least two antibodies to an antigen. Typically, the different antibodies bind different epitopes. "Oligoclonal antibody" refers to a preparation of 3 to 100 different antibodies to an antigen. Typically, the antibodies in such a preparation bind to a range of different epitopes. "Polyclonal antibody" refers to a preparation of more than 1 (two or more) different antibodies to an antigen. Such a preparation includes antibodies binding to a range of different epitopes.

"Recombinant human antibody" includes human sequence antibodies that are prepared, expressed, created or isolated by recombinant means, such as antibodies isolated from an animal (e.g., a mouse) that is transgenic for human immunoglobulin genes (described further below); antibodies expressed using a recombinant expression vector transfected into a host cell, antibodies isolated from a recombinant, combinatorial human antibody library, or antibodies prepared, expressed, created or isolated by any other means that involves splicing of human immunoglobulin gene sequences to other DNA sequences. Such recombinant human antibodies have variable and constant regions (if present) derived from human germline immunoglobulin sequences. Such antibodies can, however, be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

Detection and Quantitation of Disease Marker RNA for analyses of Cancer Malignancy, Neurologic, Autoimmune, Inflammatory, Cardiovasular, Atherosclerotic, or Infectious Disease in Animal Tissues Methods are provided which include administering at least one compound to an animal, collecting a sample of at least a portion of tissue containing at least one tissue RNA from the animal, and determining at least one characteristic of the at least one tissue RNA in the collected sample. The at least one characteristic of the tissue RNA can be detection of the presence of a disease marker or a tumor marker in the tissue, or detecting a spatial or temporal change in the level of the disease marker or the tumor marker in the tissue. Tumor marker RNA can be detected and quantified for analysis of cancer or malignancy by any of a number of known techniques, including those described herein and known in the art, for example, gel electrophoresis, ELISA assay, hybridization; Northern blot; electrochemiluminescence; chromatography or quantitative PCR. Disease markers include, but are not limited to, markers for infectious disease, neoplastic disease, autoimmune disease, inflammatory disease, cardiovascular disease, atherosclerotic disease, or neurological disease.

A ribonuclease-binding molecule is administered to an animal, or subject, to be studied. Alternatively, a RNA-binding molecule is administered to the animal or subject. Alternatively, a composition including both a ribonuclease-binding molecule and a RNA-binding molecule is administered to the animal or subject. A tissue sample then is obtained from the animal or subject. RNA or cDNA isolated as described herein can be amplified or signal amplified using a method including, but not limited to: polymerase chain reaction; reverse transcriptase polymerase chain reaction; ligase chain reaction; branched DNA signal amplification; amplifiable RNA reporters; Q-beta replication; transcription-based amplification; isothermal nucleic acid sequence replication assay; boomerang DNA amplification; strand displacement activation; cycling probe technology; or a combination or variation thereof that amplifies the RNA or cDNA.

Amplified or signal-amplified RNA or cDNA can be detected by methods including, but not limited to: an electrophoresis-based detection method; ELISA detection methods using biotinylated or other modified primers; immunological detection methods using monoclonal antibodies; detection methods using a labeled fluorescent or chromagenic probe; Southern blot analysis; electrochemiluminescence; dot blot detection using a labeled probe; reverse dot blot detection; or high-performance liquid chromatography. See, e.g., U.S. Patent Publication 2006/0228732, incorporated herein by reference.

The one or more RNAs isolated and amplified may be associated with a malignancy or other pathological condition and can be a mRNA that encodes a biomarker or tumor marker. Tumor markers can be detected and quantified for use in diagnosis and/or assessment of disease progression and treatment efficacy. A tumor marker is at least one molecule that is expressed exclusively or at elevated levels in tumor tissue or cells. Tumor markers and/or the mRNA that encode these tumor markers can be released from a tumor into the blood or other bodily fluids. A number of tumor associated markers have been identified such as, for example, CA 125 (ovarian cancer), CA 15-3 (breast cancer), carcinoembryonic antigen (CEA; ovarian, lung, breast, pancreas, and gastrointestinal tract cancers), and prostate specific antigen (PSA; prostate cancer). RNA extracted from a bodily tissue can be assessed for the presence of various tumor associated mRNAs including, but not limited to, mRNA encoding mutated oncogenes or mutated DNA such as H-ras, K-ras, N-ras, c-myc, her-2-neu, bcr-abl, fms, src, fos, sis, jun, erb-B-1, Von Hippel-Lindau (VHL), PML/RAR, AML1-ETO, EWS/FLI-1, EWS/ERG; mRNA encoding tumor suppressor genes such as p53, retinoblastoma (RB), mutated-in-colon-cancer (MCC), APC, DCC, NF1, WT; mRNA encoding tumor-associated proteins elevated in certain cancers such as alpha-feto protein (AFP), CEA, TAG-72, CA 19-9, CA-125, PSA, CD44, cyclooxygenase 2 (COX-2) and beta human chorionic gonadotropin (HCG); mRNA encoding tumor-derived protein not normally found circulating in blood such as tyrosinase mRNA, keratin 19 mRNA; mRNA encoding tumor-specific antigens, such as in MAGE 1, MAGE 2, MAGE 3, MAGE 4, GP-100, and HAGE 6, MUC 18, p97; mRNA encoding other tumor markers such as p16, TEP1, human telomerase RNA template (hTR), MART-1, bax, suvivin, epidermal growth factor receptor (EGFR), epidermal growth factor (EGF), 5T4, DNA methyltransferase, matrix metalloproteinases, mammaglobin, DDC(PCA3), glutathione S-transferase, MDR-1, JC virus; and mRNA or messenger-like RNA associated with ribonucleoproteins and RNA within ribonucleoproteins such as telomerase RNA, and RNA associated with heterogenous nuclear ribonucleoprotein A1 (hn RNP-A1) and A2/B1 (hn RNP-A2/B1) complexes, and heterogenous nuclear ribonucleoprotein K (hn RNP-K), such as c-myc oncogene RNA (see, e.g., U.S. Patent Publications 2005/0003440; 2006/0228729, which are incorporated herein by reference).

The presence or absence of RNA in a bodily fluid or tissue can be used to diagnose and monitor non-cancerous physiological states or conditions such as, for example, infectious disease, neurological, autoimmune, atherosclerotic, inflammatory, cardiovascular, metabolic, gastrointestinal, and/or urogenital conditions. For example, fetal RNA of placental origin can be detected in the maternal circulation and can be used for noninvasive prenatal monitoring for conditions such as, for example, preeclampsia and fetal aneuploidy (see, e.g., U.S. Pat. No. 6,664,056; Chiu et al., Clin. Chem. 52:313-316, 2006, which are incorporated herein by reference). In another example, the recent onset of schizophrenia in an individual can be correlated with detectable levels of human endogenous retroviral (HERV) RNA in the cerebrospinal fluid (see, e.g., Karlsson, et al., Proc. Natl. Acad. Sci. USA. 98:4634-4639, 2001, which is incorporated herein by reference). Biomarkers for other neurological diseases such as, for example, Alzheimer's disease, Parkinson's disease, and amyotrophic lateral sclerosis (ALS) have been described and include, but are not limited to, beta-amyloid, tau, synuclein, orexin, transthyretin, cystatin C, carboxy-terminal fragment of neuroendocrine protein 7B2 (see, e.g., U.S. Pat. Nos. 6,465,195 and 7,256, 003; U.S. Patent Publication 2007/0099203A1; Ranganathan, et al., J. Neurochem. 95:1461-1471, 2005; Mitchell, et al., Brain. 127:1693-1705, 2004, which are incorporated herein by reference). Biomarkers for inflammatory diseases such as, for example, sepsis and multiple sclerosis have also been described and include, but are not limited to, plasminogen activator inhibitor 1 (PAI-1), soluble thrombomodulin (sTM), interleukin 6 (IL-6), IL-10, IL-8, protein C, thrombin activatable fibrinolysis inhibitor (TAFI), protein S, antithrombin, and TNF-alpha (see, e.g., Kinasewitz, et al., Critical Care, 8:R82-R90, 2004; Bielekova & Martin, Brain, 127: 1463-1478, 2004, which are incorporated herein by reference). Biomarkers that detect CSF oligoclonal banding are indicative of inflammation-related substances in the cerebrospinal fluid (CSF). Oligoclonal bands are produced by immunoglobulins in the CSF, which suggest inflammation of the central nervous system. The presence of oligoclonal bands can indicate the presence of multiple sclerosis in the animal, subject, or patient.

Biomarkers for cardiovascular conditions such as, for example, stroke and atherosclerosis have been described and include, but are not limited to, interleukin 6 (Il-6), soluble intercellular adhesion molecule 1 (sICAM-1), serum amyloid, apolipoprotein B-100 (Apo B), C-reactive protein (CRP), PARK7, and nucleotide diphosphate kinase A (NDKA) (see, e.g., Allard, et al., Clin. Chem. 51:2043-2051, 2005; Fach, et al., Mol. Cell. Proteomics, 3:1200-1210, 2004; Revkin, et al., Pharmacol. Rev. 59:40-53, 2007, which are incorporated herein by reference). As such, RNA encoding a biomarker, for example, can be used to diagnose and monitor a disease or condition.

The presence in a bodily fluid or tissue of RNA derived from a pathogen can be used to assess infection with an infectious agent such as, for example, virus, bacteria, fungus or parasite. In general, extracellular RNA from a pathogen may arise from either disruption or lysis of the pathogen in the extracellular space or the lysis of an infected cell or the combination thereof. For example, bacterial RNA can be derived from phagocytosed bacteria or lysis of bacteria in the extracellular space and may contribute to the inflammatory response in bacterial infection (see, e.g., Kanneganti, et al., Nature, 440:233-236, 2006, which is incorporated herein by reference).

Alternatively, infection with a pathogen such as, for example, virus, bacteria, fungus, or parasite can be detected and managed therapeutically based on analysis of biomarker-associated mRNA generated by the host in response to infection. For example, a number of biomarkers associated with inflammation and coagulation exhibit significant correlations relative to increasing severity of bacterial-induced sepsis including plasminogen activator inhibitor 1 (PAI-1), soluble thrombomodulin (sTM), interleukin 6 (IL-6), IL-10, IL-8, protein C, thrombin activatable fibrinolysis inhibitor (TAFI), protein S, antithrombin, and TNF-α (see, e.g., Kinasewitz, et al., Critical Care 8:R82-R90, 2004, which is incorporated herein by reference).

TABLE 1

Disease Markers

| Disease | Potential Biomarkers* |
|---|---|
| Cancer | H-ras, K-ras, N-ras, c-myc, her-2-neu, bcr-abl, fms, src, fos, sis, jun, erb-B-1, Von Hippel-Lindau (VHL), PML/RAR, AML1-ETO, EWS/FLI-1, EWS/ERG, p53, retinoblastoma, mutated-in-colon-cancer (MCC), APC, DCC, NF1, WT, alpha-feto protein (AFP), CEA, TAG-72, CA 19-9, CA-125, PSA, CD44, cyclooxygenase 2 (COX2), beta human chorionic gonadotropin (HCG), tyrosinase, keratin 19, MAGE1, MAGE2, MAGE3, MAGE4, GP-100, HAGE 6, MUC 18, p97, p16, TEP, human telomerase RNA template (hTR), MART-1, bax, surviving, EGFR, EGF, 5T4, DNA methyltrasnferase, matrix metalloproteinases, mammaglobin, DDC (PCA3), glutathione S-transferase, MDR-1, human telomerase reverse transcriptase (hTERT) |
| Bladder cancer | v-ets erythroblastosis virus E26 oncogene homolog 2 (ETS2), urokinase plasminogen activator (uPa) |
| Breast cancer | CA 15-3, CEA, COX-2, Her2/Neu, Bcl-2 |
| Colon cancer | Mutated-in-colon-cancer (MCC), CEA, COX-2, CA19-9 |
| Liver cancer | hTERT, AFP |
| Lung cancer | CEA |
| Melanoma | Tyrosinase, Melan A, MAGE3, bRAF, nRas, CDK4, CCND1, Rab38, p21, p16, BCL-6, Ki-67, ERK-1, ERK-2, CCR4, CCR7, CCR10, melastatin, MITF, galectin-3, β-catenin, IL-6 receptor, STAT1/STAT3, PTEN, AKT, TA90, osteopontin, MCAM, AP-2, CBP, FOXP3, CD3, CD4, TIA1, MDA-7, VEGFA, VEGFC, D2-40, HIF-1, CD9, TM4SF, cKIT |
| Ovarian cancer | CA-125, CEA |
| Pancreatic cancer | CEA |
| Prostate cancer | PSA |
| Neurological conditions | |
| Schizophrenia | Human endogenous retroviral (HERV) RNA |
| Alzheimer's disease | Beta-amyloid, tau, ADAM9, APH1A, BACE1, BACE2, CTSB, NCSTN, PSEN1, PSEN2, IDE, PLAT, PLAU, PLG, APLP1, APP, LRP1, LRP6, LRP8, A2M, ACHE, APBB1, APBB2, APO-E, BCHE, UBQLN1, |

TABLE 1-continued

Disease Markers

| Disease | Potential Biomarkers* |
|---|---|
| | MAP2, MAPT, PKP4, PRKCI, APBA1, CHAT, BDNF, ABCA1, APO-A1, CLU, HADH2, INS, LPL, SNCB, CASP3, CASP4, ERN1, PRKCA, PRKCE, IL1A, MPO, PRKCZ, SNCA, APPBP1, EP300, CDC2, CDK5, CDKL1, GSK3A, GSK3B, INSR, PRKCB1, PRKCD, PRKCG, PRKCQ, APLP2, GNAO1, GNAZ, GNB1, GNB4, GNB5, GNG10, GNG11, GNG3, GNG4, GNG5, GNG7, GNG8, GNGT1, GNGT2, APBA3, PPBP1, GAP43, GNB2, UQCRC1, UQCRC2, CTSC, CTSD, CTSG, CTSL, UQCRC2, SERPINA3 |
| Parkinson's disease, ALS | synuclein, orexin, transthyretin, cystatin C, carboxy-terminal fragment of neuroendocrine protein 7B2 |
| Inflammation | Plasminogen activator inhibitor 1 (PAI-1), soluble thrombomodulin (sTM), interleukin 6 (LI6), IL8, IL10, protein C, thrombin activatable fibrinolysis inhibitor (TAFI), protein S, antithrombin, TNF-alpha |
| Cardiovascular | |
| Stroke | PARK7, nucleotide diphosphate kinase A (NDKA) |
| Atherosclerosis | IL-6, soluble intracellular adhesion molecule 1 (sICAM-1), serum amyloid, apolipoprotein B-100 (Apo B), C-reactive protein |
| Renal dysfunction | Wilm's tumor suppressor gene WT1, FOXP3 |

*Detection of nucleic acids for a combination of one or more of these biomarkers may be indicative of a disease state.
*Each potential biomarker may be indicative of one or more cancer type or other disease state.

Determining Characteristics of Animal Tissue Related to Detection or Diagnosis of Disease Malignancy The methods described herein identify humans or animals bearing or at risk for developing malignancies including, but not limited to, tumors of breast, ovarian, lung, cervical, colorectal, gastric, pancreatic, bladder, endometrial, head and neck, brain, kidney, and esophageal tissues, as well as leukemias, lymphomas, melanoma, and sarcomas. The methods described herein may further be utilized to identify humans or animals with premalignancy, including, but not limited to, colorectal adenoma, cervical dysplasia, cervical intraepithelial neoplasia (CIN), bronchial dysplasia, bronchial metaplasia, atypical hyperplasia of the breast, ductal carcinoma in-situ of the breast, atypical endometrial hyperplasia, prostatic intraepithelial neoplasia, and Barrett's esophagus. The methods described herein can be applied to a subject of any age, race, ethnicity or gender, although it is preferred that the reference group or population include individuals of similar age (child, adult, elderly) and sex (male, female). The methods permit detection, diagnosis, and monitoring of disease, particularly cancer and premalignancy, and identification of individuals at risk for developing disease, particularly cancer or neoplastic disease such as premalignancy, providing considerable clinical utility. Methods are provided to identify, stratify, or select a human or animal that might benefit from a therapy, or from a further diagnostic test. Utilization of these methods permits disease such as cancer to be monitored, including response to cancer therapies, by providing a marker to guide whether therapeutic effect has been achieved, or if more therapy is required, and to assess prognosis.

The terms "tumor-associated," "disease-associated," "disease-related," "tumor-related" and "non-tumor-related" include particular RNA species, as well as total extracellular RNA. Certain RNA species, such as oncogenic RAS, p53, and other RNA species, are associated with the existence of cells comprising a disease state, particularly a neoplastic disease, malignancy or premalignancy. RNA species are "tumor-associated," "disease-associated," "disease-related," or "tumor-related" when their presence or level as a component of total extracellular RNA is indicative of the existence of a disease, particularly a neoplastic disease. "Non-tumor-related" RNA species, on the other hand, comprise RNA species component (s) present in healthy individuals; but such species may also be present in individuals bearing disease-associated, disease-related, or tumor-related extracellular RNA species as well. In certain embodiments, detecting a lack of expression or expression of a normal level of an RNA species comprising non-tumor-related RNA may further indicate the existence of disease in said human or animal.

The term "RNA species" refers to RNA selected from one or more of the group comprising messenger RNA, inhibitory RNA, coding RNA, non-coding RNA, RNA having a sequence complimentary to a mutated or altered DNA, RNA having a sequence complimentary to non-mutated DNA, and ribonucleoprotein RNA. Further, RNA species may be disease-associated, tumor-associated, disease-related, tumor-related, and non-tumor-related.

Detection and Quantification of RNA from Animal Tissues

Extraction of RNA from Animal Tissue. Tissue RNA can be extracted from a variety of bodily fluids including, but not limited to, blood, plasma, serum, urine, saliva, cerebrospinal fluid (CSF), semen, gastrointestinal secretions, cervical secretions, breast secretions, sweat, and bronchial lavage. For example, tissue RNA can be extracted from a cellular serum or plasma isolated from whole blood. Blood is drawn using standard methods into a collection tube such as a BD Vacutainer® Blood Collection Tube in the presence (plasma) or absence (serum) of an anticoagulant agent such as for example heparin, EDTA, or sodium citrate. Plasma or serum can be fractionated from whole blood by centrifugation, using preferably gentle centrifugation at 300-800×g for five to ten minutes, or fractionated by other standard methods. Centrifugation results in pelleting of the blood cells to bottom of the tube and enables extraction of the a cellular plasma or serum from the upper layer. As extracellular RNA can be associated with apoptotic bodies, high centrifugation rates are preferably avoided to prevent fractionating out apoptotic bodies with the cells. The volume of fluid required for RNA extraction may vary from for example 100 microliters to 10 milliliters or more depending upon the clinical intent, the relative abundance of the target RNA and whether or not an amplification step is including in the protocol.

RNA can be extracted from a bodily fluid using methods or modifications of methods commonly used for extraction of mammalian intracellular RNA or viral RNA. Methods or modifications of methods commonly used for extraction of RNA include, but are not limited, to gelatin extraction; silica, glass bead, or diatom extraction; guanidinium thiocyanate acid phenol based extraction; guanidinium thiocyanate acid based extraction; centrifugation through cesium chloride or similar gradients; phenol-chloroform based extraction; hybridization and immunobead separation; or commercially available RNA extraction methods. For example, RNA can be extracted from a bodily fluid using a commercial isolation kit such as, for example, RNeasy Mini-Kit (Qiagen), QIAamp viral RNA Mini-kit (Qiagen), SV total RNA Isolation System (Promega), Eppendorf Perfect RNA Eukaryotic mini reagent set (Brinkman Instruments Inc.), MagnaZorb DNA mini-Prep Kit (CORTEX Biochem), and TriBD reagents (Sigma). As such, RNA isolation can be performed according to the manufacturer's instructions or modified as needed.

Alternatively, RNA can be extracted from a bodily fluid using variations on the guanidinium isothiocyanate-phenol-chloroform RNA extraction protocol originally described by Chomczynski and Sacchi (*Anal. Biochem.* 162:156-159, 1987, which is incorporated herein by reference). For example, a bodily fluid such as plasma can be added to a denaturing solution of 4 M guanidinium thiocyanate, 25 mM sodium citrate, pH 7.0, 0.5% sarcosyl, 0.1 M 2-mercaptoethanol at a ratio ranging from 1:10 to 1:1. Sequentially, 2 M sodium acetate, pH 4.0, phenol, and chloroform-isoamyl alcohol (49:1) are added, with mixing after addition of each reagent. The resultant mixture is shaken vigorously for 10 seconds, cooled on ice for 15 minutes, and then centrifuged at 10,000×g for 20 minutes at 4 degrees centigrade. The aqueous phase is mixed with isopropanol and cooled at −20 degrees centigrade to precipitate RNA. Alternatively, a premixed solution of guanidinium isothiocyanate and phenol can be used to extract RNA. For example, an equal volume of plasma can be added to a volume of 4 mol/L guanidinium isothiocyanate which has been premixed with acid phenol (1:3 ratio) and 1 ml/L Triton X-100, followed by the addition of acetic acid to a final concentration of 125 mmol/L. The aqueous phase may then be separated by addition of 1-bromo-3-chloropropane (1:10 by volume) and RNA precipitated in the presence of ammonium acetate and isopropanol (see, e.g., El-Hefnawy, et al. *Clin. Chem.* 50:3, 2004, which is incorporated herein by reference). Alternatively, a commercial monophase guanidine-thiocyanate-phenol solution can be used such as, for example, TRI Reagent™ (TRI Reagent, Sigma Trisolv™, BioTecx Laboratories, Houston, Tex., TRIzol™, GIBCO BRL/Life Technologies, Gaithersburg, Md., ISOGEN™, Nippon Gene, Toyama, Japan, RNA Stat™ 60, Tel-test, Friendsword, Tex.) according to manufacturer's directions.

In some instances, polyadenylated (poly(A)+) mRNA may be isolated from the total RNA. Poly(A)+ mRNA typically constitutes about 1% to 5% of the RNA recovered in total RNA. Poly(A)+ mRNA can be isolated using oligo(dT) selection. For example, the total RNA sample can be passed through a matrix to which oligo(dT) has been attached. The poly(A)+ mRNA binds to the oligo(dT) and non-binding ribosomal and transfer RNAs are washed away. The poly(A)+ mRNA is eluted from the oligo(dT) by reducing the buffer salt concentration. Kits for isolation of poly(A)+ mRNA are available from commercial sources (from, e.g., Promega, Madison, Wis.; Applied Biosystems/Ambion, Austin, Tex.; Stratagene, La Jolla, Calif.)

Under some circumstances, extracellular deoxyribonucleic acid (DNA) can be extracted along with RNA during the isolation process. Depending upon what methods will be used to detect the RNA and whether the sample will be subjected to amplification, it may be desirable to further purify the RNA away from the contaminating DNA. DNA can be eliminated from a RNA sample by digesting the sample with a DNA specific DNase 1 (from, e.g., Invitrogen, catalog #18068-015, Carlsbad, Calif.) as described by Rashtchian (*PCR Methods Appl.* 4:83-91, 1994, which is incorporated herein by reference).

In some instances, the extracellular RNA in the bodily fluid can be associated with particulate matter such as, for example, a protein complex, a lipid complex, a protein-lipid complex, apoptotic bodies. Apoptotic bodies are small sealed membrane vesicles that are derived from cells undergoing cell death by apoptosis. RNA associated with apoptotic bodies or other particulate matter can be isolated from a cell-free supernatant of a bodily fluid using filters ranging in pore size from 0.45 μm to 5 μm or using high speed centrifugation at 100,000×g, for example (see, e.g., Hasselmann, et al., *Clin. Chem.* 47:1488-1489, 2001; Karlsson, et al. *Proc. Natl. Acad. Sci., USA.* 98:4634-4639, 2001, which are incorporated herein by reference). The RNA associated with the filtered or pelleted material can be extracted using guanidinium isothiocyanate as described.

Quantifying RNA from Animal Tissues

Methods are provided which include administering at least one compound to an animal, collecting a sample of at least a portion of tissue containing at least one tissue RNA from the animal, and determining at least one characteristic of the at least one tissue RNA in the collected sample. The at least one characteristic of the tissue RNA can be detection of the presence of a RNA characteristic of a disease marker in the tissue, or detecting a spatial or temporal change in the level of the RNA characteristic of the disease marker in the tissue. The at least one characteristic can be a level of the at least one tissue RNA in the collected sample. The at least one characteristic can be an identity of the at least one tissue RNA associated with a disease state. The at least one characteristic can be a relative level of at least two different RNAs associated with a disease state. The at least one characteristic can be a relative level of the at least one tissue RNA measured at two or more time points. The levels of the at least one RNA or the relative levels of the RNAs can be normalized with respect to the activity of the ribonuclease inhibitor which is present in the blood or tissue of the animal, since the activity of the ribonuclease inhibitor may vary or decrease over time in the blood or tissue of the animal.

RNA isolated from a bodily fluid can be detected, assessed, and/or quantified using gel electrophoresis in combination with a staining method. For example, RNA can be separated by gel electrophoresis on a 1.0-1.5% agarose gel in formaldehyde and MOPS using standard procedures. An intercalating dye such as, for example, ethidium bromide can be used to stain the agarose gel either during or at the completion of electrophoresis. Analysis of the gel under a ultraviolet lamp allows for detection of the separated RNA in the agarose gel, primarily the 18S and 28S ribosomal RNA. The integrity of the 18S and 28S bands can be used as a measure of the relative quality of the total RNA.

Alternatively, RNA isolated from a bodily tissue or fluid can be detected, assessed, and/or quantified using ion-pair reversed-phase high performance liquid chromatography (IP RP HPLC). For example, RNA can be chromatographed using IP RP HPLC under fully denaturing conditions in triethylammonium acetate (TEAA) at 70° C. using DNASep® cartridges and variable gradient conditions (see, e.g., Azaranin & Hecker, *Nucleic Acids Res.* 29:e7, 2001, which is incorporated herein by reference). In this manner it is possible to distinguish between the 18S and 28S ribosomal RNAs and smaller RNA species or degraded RNA. In some instances, IP RP HPLC can be used to isolate specific populations of RNA such as, for example, transfer RNAs and other small RNAs, specific ribosomal RNAs, and/or mRNAs of a specific size range (see, e.g., Dickman & Hornby, *RNA,* 12:691-696, 2006, which is incorporated herein by reference).

Specific mRNA transcripts in a total RNA or poly(A)+ mRNA preparation can be detected, assessed, and/or quantified using a variety of hybridization methods with appropriate complimentary probes. For example, a specific mRNA transcript can be detected using Northern analysis in which total RNA or poly(A)+ mRNA is separated on a formaldehyde agarose gel as described above, transferred to a membranous substrate such as nylon or nitrocellulose, for example, and subsequently hybridized with a labeled probe. The probe can be anti-sense RNA, complimentary single stranded DNA, an oligonucleotide, an aptamer, or a protein nucleic acid (PNA), for example. The probe can be labeled with a radioactive tag such as, for example, $^{32}$P or $^{35}$S and as such hybridization is detected using autoradiography. Alternatively, the probe can be labeled with digoxigenin (DIG) or biotin, for example, and as such hybridization is detected using immunological techniques in combination with colorimetric or chemiluminescence methods. Alternatively, the probe can be labeled with a fluorescent tag such as fluorescein, rhodamine, Cy3 Cy5 and/or quantum dots, for example.

Alternatively, specific mRNA transcripts in a total RNA or poly(A)+ mRNA preparation can be detected, assessed, and/or quantified using RNase protection assays in which total RNA or poly(A)+ mRNA is hybridized in solution with a labeled probe of uniform length. Once the RNA/probe duplex has been formed, the sample is treated with RNase to eliminate single stranded or non-bound RNA. The resulting RNA/probe duplex is detected based on the label associated with the probe. For example, a $^{32}$P-labeled probe can be hybridized to total RNA, treated with RNase, chromatographed, and detected by autoradiography.

Other hybridization methods such as microarrays, for example, can be used to detect, assess, and/or quantify specific transcripts and will be discussed below in the context of amplification of mRNA transcripts.

In some instances, an mRNA transcript or transcripts can be present at a level in a bodily tissue or fluid that is below the level of detection of the detection methods described above. As such, the mRNA transcripts can be amplified using a variety of amplification methods such as, for example, polymerase chain reaction (PCR), reverse transcriptase polymerase chain reaction, ligase chain reaction, branched DNA signal amplification, amplifiable RNA reporters, Q-beta replication, transcription based amplification, isothermal nucleic acid sequence replication assay, boomerang DNA amplification, strand displacement activation, cycling probe technology, or a combination or variation thereof that amplified RNA or cDNA.

RNA can be amplified using a combination of reverse transcription to form an intermediary cDNA followed by in vitro transcription back to RNA using the cDNA as template. The RNA is reverse transcribed using random primers or oligo(dT) primers to generate a corresponding cDNA sequence. Random primers will amplify all the RNA in the sample including that from messenger RNA (mRNA), transfer RNA, ribosomal RNA, and other non-mRNA. In contrast, oligo dT primers hybridize with the 3' poly(A) tail of mRNA, resulting in amplified RNA primarily from mRNA. The resulting cDNA is then subjected to in vitro transcription. Thousands of RNA transcripts can be generated by in vitro transcription from one cDNA. In this way, RNA isolated from a bodily fluid can be uniformly amplified. Kits for RNA amplification are available from commercial sources (from, e.g., Invitrogen, Carlsbad, Calif.).

Amplified RNA generated in this way can be used for expression profiling using a microarray such as, for example, Affymetrix GeneChips® (from, e.g., Affymetrix, Santa Clara, Calif.). The amplified products are hybridized to short DNA fragments chemically synthesized at specific locations on a coated quartz surface. The precise location where each probe is synthesized is called a feature, and millions of features can be contained on one array. The amplified RNA can be labeled during in vitro translation either directly with a fluorescent dye or with biotin that is reacted post-hybridization with streptavidin-conjugated fluorescent dye. The microarrays are subsequently scanned by fluorescence spectroscopy and relative expression of various RNA transcripts in the sample can be quantified.

Polymerase chain reaction (PCR) in combination with reverse transcriptase can be used to amplify specific RNA transcripts. PCR uses one or more pairs of 5' and 3' primers to synthesis or amplify very specific regions of a transcript. As above, total RNA is subjected to reverse transcription using either random or oligo(dT) or a combination of primers to generate cDNA. The resulting cDNA can be used for PCR with specific primers. The primers can be designed to amplify all or part of the nucleotide sequence of a specific tumor marker or other disease marker, for example. For some applications or detection schemes, PCR can be done in the presence of labeled nucleotides. Nucleotides can be labeled with a radioisotope such as $^{32}$P or $^{35}$S, for example. Alternatively, nucleotides can be labeled with biotin or digoxigenin or with a fluorescent dye such as Cy3 or Cy5, for example.

The resulting amplified PCR product or products can be detected using a variety of methods such as, for example, gel electrophoresis; ELISA (Enzyme-Linked ImmunoSorbent Assay) and modifications thereof using biotinylated or otherwise modified primers and/or oligonucleotides; hybridization techniques using radiolabeled, fluorescently labeled, and/or chromogenically-labeled probes; electrochemiluminescence, high-performance liquid chromatography, reverse dot blot detection; Southern blot analysis; Northern blot analysis; and flow cytometry (see, e.g., Lazar *Genome Res.* 4:1-14, 1994, which is incorporated herein by reference). For example, the PCR product can be chromatographed by gel electrophoresis and either directly stained with ethidium bromide or transferred to a membrane and detected with a labeled probe as described herein. Alternatively, PCR products generated in the presence of a radiolabeled nucleotide can be separated by gel electrophoresis and detected by autoradiography, for example.

ELISA methods may also be used to detect PCR products. In this instance, PCR can be carried out in the presence of labeled nucleotides and/or labeled PCR primers such that the resulting PCR products are able to bind to a substrate coating a multi-welled, microtiter plate and can be detected using fluorescence, immunofluorescence, chemiluminescence or colorimetric spectroscopy. For example, PCR can be carried out in the presence of biotinylated nucleotide and a 5' and/or 3' primer containing an immunogenic species such as FITC or digoxigenin. The resulting biotinylated PCR product can be bound to a streptavidin-coated surface and can be detected using horseradish peroxidase-conjugated antibodies to either FITC or digoxigenin, a chromogenic substrate, and a spectroscopic plate reader, for example. Alternatively, one or more PCR product can be detected using methodologies based on traditional ELISA but with added multiplexing capabilities and chemiluminescence or electrochemiluminescence detection systems such as, for example, FAST Quant® (Whatman, Kent, UK), MesoScale® (MesoScale, Gaithersburg, Md.), and Searchlight® (Thermo Fisher Scientific, Waltham, Mass.).

Real-time quantitative PCR (RT-qPCR) can be used to quantify expression of RNA by detecting PCR products in real time as they are synthesized. RT-qPCR integrates a PCR-based assay with laser scanning technology to excite fluorescent dyes present in the sample and can be probe-based or intercalator-based, for example. Probe-based RT-qPCR uses a pair of unlabeled PCR primers and an additional fluorogenic oligonucleotide probe which has both a reporter fluorescent dye and a quencher dye attached and is exemplified by Taq-Man®. Intercalator-based RT-qPCR uses an intercalating dye in the PCR reaction which binds to newly synthesized double-stranded DNA and is exemplified by SYBR® Green. Various integrated systems are available for performing RT-qPCR including, but not limited to, the LightCycler® System (Roche Applied Science, Indianapolis, Ind.), and the 7900HT Real-Time PCR System (Applied Biosystems, Foster City, Calif.). Alternatively, RT-qPCR can be performed on a microchip dynamic array system as exemplified by the BioMark™ Dynamic Array System (see, e.g., Spurgeon, et al. *PLoS ONE* 3:e1662, 2008, which is incorporated herein by reference).

RNA or cDNA derived from a RNA transcript also may be amplified using a variety of isothermal methods in which a thermocycler is not required. Isothermal amplification methods include, but are not limited, to transcription mediated amplification, nucleic acid sequence-based amplification, signal mediated amplification of RNA technology, strand displacement amplification, rolling circle amplification, loop-mediated isothermal amplification of DNA, isothermal multiple displacement amplification, helicase-dependent amplification, single primer isothermal amplification, and circular helicase-dependent amplification (see, e.g., Gill & Ghaemi, *Nucleosides, Nucleotides, and Nucleic Acids.* 27:224-243, 2008, which is incorporated herein by reference). In some instances, the RNA may first be reverse transcribed into cDNA prior to the initiation of an isothermal amplification method. In other instances, the RNA can be amplified through a DNA intermediary. For example, a specific RNA can be directly amplified using the nucleic acid sequence-base amplification method. A RNA template is selectively targeted with an antisense primer and the complement DNA is extended by reverse transcription. The RNA-DNA hybrid is treated with RNase H to eliminate the RNA template. A sequence selective sense primer with T7 promoter sequence is targeted to the DNA strand and extended by reverse transcription. The double stranded DNA with the T7 promoter becomes a self-sustaining template for RNA synthesis using the T7 RNA polymerase. Detection systems and methods such as those described above can be used to detect and quantify the products of isothermal amplification.

One or more specific RNA targets can be detected using molecular beacons and fluorescence resonance energy transfer (FRET). Molecular beacons are dual labeled compounds a donor fluorophore at one end and an acceptor fluorophore or quencher at the other end. The molecular beacon can be an oligonucleotide RNA or DNA based aptamer. Alternatively, the molecular beacon can be a protein based compound such as, for example, an antibody or other protein designed to bind RNA. Upon binding of a specific target, the molecular beacon undergoes a conformational shift such that the distance between the donor fluorophore and the acceptor fluorophore or quencher is altered, leading to a change in measurable fluorescence. This phenomenon is referred to as fluorescence resonance energy transfer (FRET). FRET is a distance-dependent interaction between the electronic excited states of two dye molecules in which excitation is transferred from a donor molecule to an acceptor molecule without emission of a photon. In some instances, interaction of a donor molecule with an acceptor molecule may lead to a shift in the emission wavelength associated with excitation of the acceptor molecule. In other instances, interaction of a donor molecule with an acceptor molecule may lead to quenching of the donor emission. As such, a molecular beacon can be used to monitor changes in the fluorescent properties of the molecular beacon in response to binding a specific RNA species. In some instances, the molecular beacon can be directly injected into an animal and the change in fluorescence signal upon binding a specific RNA measured transdermally. An external device for transdermal measurement of fluorescence in the peripheral circulation has been described in U.S. Pat. No. 6,663,846, which is incorporated herein by reference. As such, the device may periodically emit electromagnetic energy sufficient to excite the fluorophores associated with, for example, an aptamer or antibody on a modified red blood cell and as such measure emitted fluorescence. Alternatively, the molecular beacon can be used externally to detect extracted RNA and/or amplified cDNA using fluorescence spectroscopy.

RNA or cDNA derived from a RNA transcript can be detected using nucleic acid-based electrical detection systems. In this instance, electrical biosensors are used to convert a base-pair recognition event into a useful electrical signal. A number of electrical parameters can be used to detect binding of a specific RNA or cDNA to a reactive substrate such as, for example, voltage, current, conductance/resistance, impedance, and capacitance (see, e.g., Gabig-Ciminska *Microbial Cell Factors* 5:9, 2006, which is incorporated herein by reference). For example, a probe or probes that bind specific RNA and/or cDNA are attached to a surface such as a biochip or microbeads. The probe can be a complementary oligonucleotide sequence, an oligonucleotide binding protein such as an antibody, or an oligonucleotide binding protein nucleic acid (PNA), for example. Upon binding the target RNA or cDNA, a transducer converts the biological interaction into a measurable signal that can be proportional to the degree of hybridization and reflective of the quantity of target in the sample.

In some instances genetic polymorphisms or somatic mutations can be assessed in one or more RNAs extracted from a bodily fluid or tissue, as such differences can be correlated with a specific disease state. For example, somatic missense or truncation mutations in the beta-catenin RNA cause the loss of a regulatory site within the encoded protein and are observed in 25% of human hepatocellular carcinomas (see, e.g., de La Coste, et al., *Proc. Natl. Acad. Sci. USA.* 95:8847-8851, 1998, which is incorporated herein by reference). As such, genetic polymorphisms or mutations in the RNA can be assessed using a variety of methods such as, for example, direct DNA sequencing of reverse transcribed-PCR products, PCR in combination with denaturing gradient gel electrophoresis, PCR in combination with automated fluorescence/RNA-based dideoxy fingerprinting, and hybridization with mutation specific hybridization probes (see, e.g., de La Coste, et al., *Proc. Natl. Acad. Sci. USA.* 95:8847-8851, 1998; Martincic, et al., *Oncogene,* 18:617-621, 1999, which are incorporated herein by reference).

Detection and Quantitation of Housekeeping RNAs. Analysis of one or more housekeeping gene mRNA transcripts can be carried out in conjunction with analysis of one or more RNA associated with a tumor and/or other disease state. Housekeeping gene products are required for the maintenance of basal cellular function and are constitutively expressed in all human cells, for example, and as such can be used to calibrate measurements of gene expression. A number of housekeeping genes have been described including, but not limited to, 18S ribosomal RNA, beta actin, glyceraldehyde-3-phosphate dehydrogenase, phosphoglycerate kinase 1, peptidylprolyl isomerase A (cyclophilin A), ribosomal protein L13a, ribosomal protein, large, P0, beta-2-microglobulin, tyrosine 3-monooxygenase/tryptophan 5-monooxygenase activation protein, zeta polypeptide, succinate dehydrogenase, transferrin receptor (p90, CD71), aminolevulinate, delta-, synthase 1, beta glucuronidase, hydroxymethyl-bilane synthase, hypoxanthine phosphoribosyltransferase 1, TATA box binding protein, beta tubulin (see, e.g., Eisenberg & Levanon, *Trends Genet.* 19:362-365, 2003, which is incorporated herein by reference). Detection and quantitation of housekeeping genes and disease marker genes are used to measure relative levels of disease marker genes in a subject to determine the presence of disease in the subject. Detection and quantitation can be carried out by a number of techniques as described above including, but not limited to, HPLC, Northern blot analysis, RNase protection, microarrays, reverse transcription, polymerase chain reaction, ELISA, real-time quantitative PCR, molecular beacons, fluorescence resonance energy transfer (FRET), or nucleic acid based electrical detection.

Ribonuclease Inhibitors

Methods are described herein which include administering at least one compound to an animal, wherein the at least one compound is configured to prevent the cleavage of at least one tissue RNA by a ribonuclease (RNase). RNase is an enzyme class that catalyzes the hydrolysis of RNA into smaller components. RNases are ubiquitous, found in most organisms and in many organs and bodily fluids. Examples of RNases include, but are not limited to, RNases A, B, and C, members of the mammalian ribonuclease A super family, RNase 1 (e.g., human pancreatic), RNase 2 (eosinophil-derived neurotoxin), RNase 3 (eosinophil-cationic protein), RNase 4 (liver type), RNase 5 (angiogenin), RNase 6, RNase 7, RNase 8, RNase H, RNase L (innate immune system), RNase P (nuclear) as well as the bacterial RNases I, II, III, P, PH, R, D, T, BN, E, and M, among others. All share the primary activity of degrading RNA. For a more extensive discussion of RNases, see, for example Beintema. *Cell. Mol. Life Sci.* 54:763-765,1998; Beintema & Kelineidam, *Cell. Mol. Life Sci.* 54:825-832, 1998; Spencer, et al., *J. Pharmacol. Exp. Ther.* 301:325-329, 2002; Rudolph, et al., *Antimicrob. Agents Chemother.* 50:3194-3196, 2006, which are incorporated herein by reference).

A ribonuclease binding molecule can be used to stabilize RNA by inhibiting the activity of RNases. A ribonuclease binding molecule for in vivo stabilization of RNA can be, for example, a protein, a small molecule, an aptamer, an antibody, a nucleotide derivative, or an oligonucleotide. Several naturally-occurring RNase inhibitor proteins have been identified. The human placental RNase inhibitor has been extensively characterized. This approximately 50 kDa protein was originally isolated from human placenta but has been detected in a number of tissues and cell types including, for example, brain, liver, testes, and erythrocytes (see, e.g., Moenner, et al., *Blood Cells, Molecules Diseases.* 24:149-164, 1998, which is incorporated herein by reference). The human placental RNase inhibitor inhibits RNases related to pancreatic RNase A and is the basis for RNasin®, a reagent used in laboratory settings during isolation and manipulation of RNA to prevent degradation (from, e.g., Promega Corporation, Madison, Wis.). SUPERase In™ is another example of a ribonuclease inhibitor protein that inhibits RNase A as well as RNase B, RNase C, RNase T1, and RNase 1 (from, e.g., Ambion, Inc., Applied Biosystems, Foster City, Calif.).

A ribonuclease inhibitor protein for use in stabilizing RNA in vivo can be purified from a natural source such as human placenta (Blackburn, *J. Biol. Chem.,* 252: 5904-5910, 1977; Blackburn, *J. Biol. Chem.,* 254: 12484-12487, 1979; Blackburn and Moore, *The Enzymes, vol. XV, Nucleic Acids, Part B*, Ed., Academic Press, pp. 416-424 (1982), which are incorporated herein by reference). Alternatively, a ribonuclease inhibitor protein such as the human placental RNase inhibitor can be generated using standard recombinant molecular biology techniques as described in U.S. Pat. No. 5,552,302, which is incorporated herein by reference. The full-length coding sequence for RNase inhibitor proteins such as for example the placental RNase inhibitor and the RNase L inhibitor are available in GeneBank and as such can be used as a starting point for cloning and expression of a ribonuclease inhibitor protein. Alternatively, full-length cDNA clones of a ribonuclease inhibitor protein such as, for example, the placental ribonuclease inhibitor may be available from a commercial source (from, e.g., Origene, Rockville, Md.). RNase inhibitor protein preparations are also available from a variety of commercial sources (from, e.g., Invitrogen, Carlsbad, Calif.; Sigma-Aldrich, St. Louis, Mo.; Stratagene, La Jolla, Calif.).

In some instances, the ribonuclease binding molecule can be a small molecule. For example, oligo(vinylsulfonic acid) inhibits RNAse A catalysis in a salt-dependent manner with inhibition constants ($K_i$) ranging from approximately 10 picomolar to 120 nanomolar in 0 to 100 mM sodium chloride (see, e.g., Smith, et al. *J. Biol. Chem.* 278:20934-20938, 2003, which is incorporated herein by reference). Similarly, pyrophosphate-linked oligonucleotides have been shown to inhibit RNase activity (see, e.g., Russo & Shapiro, *J. Biol. Chem.* 274:14902-14908, 1999, which is incorporated herein by reference). For example, 5'-phosphor-2'-deoxyuridine 3'-pyrophosphate, P'-P5-ester with adenosine 3'-phosphate (pdUppAp) has a strong binding affinity for RNase A with $K_i$ values of 27 and 240 nM at pH 5.9 and 7.0, respectively and also inhibits the activity of RNase-2 (eosinophil derived neurotoxin) and RNase-4. Other examples of small molecule RNase inhibitors derived from nucleotides include, but are not limited to, adenosine 5-pyrophosphate derivatives such as 5'-diphosphoadenosine 3'-phosphate (ppA-3'-p) and 5'-diphosphoadenosine 2'-phosphate (ppA-2'-p); diadenosine derivatives such as Ap4A and Ap5A; uridine derivatives such as 2'-fluoro-2'deoxyuridine 3'-phosphate, arabinouridine 3'-phosphate, and 3'-N'alkylamino-3'-deoxy-arauridines; inosine 5'-phosphate; and 3'-N-oxyurea-3'-deoxythymidine 5'-phosphate with zinc ion chelator (see, e.g., Yakovlev, et al. *Mol. Biol.* 40:867-874, 2006, which is incorporated herein by reference). Examples of non-nucleotide derived small molecular RNase inhibitors include, but are not limited to, 8-amino-5-(4'-hydroxybiphenyl-4-ylazo)naphthalene-2-sulfonate and similar compounds; catechins derived such as epi-gallocatechin-3-gallate derived from green tea (see, e.g., Yakovlev, et al. *Mol. Biol.* 40:867-874, 2006). Other examples of small molecular inhibitors of RNase are described in U.S. Pat. Nos. 4,966,964; 5,019,556; and 5,266,687 and U.S. Patent Publication 2007/0032418A1, which are incorporated herein by reference.

Alternatively, the ribonuclease binding molecule can be a RNA or DNA oligonucleotide-based aptamer. Aptamers specific for virtually any class of molecules can be routinely isolated from a large library of $10^{14}$ to $10^{15}$ random oligonucleotide sequences using an iterative in vitro selection procedure often termed "systematic evolution of ligands by exponential enrichment" (SELEX; Cao, et al. *Current Proteomics* 2:31-40, 2005; Proske, et al., *Appl. Microbiol. Biotechnol.* 69:367-374, 2005, which are incorporated herein by reference). Aptamers with RNase inhibitor activity can be isolated by screening an aptamer library against recombinant RNase protein immobilized on a substrate such as filters, beads or microtiter plates, isolating and amplifying bound aptamers, and repeating the screening process until aptamers with appropriate binding affinity are selected. A ribonuclease activity assay can be used to assess which of the binding aptamers are able to inhibit the activity of the enzyme. Similar methods have been used to isolate aptamer-based inhibitors (V-2, and VI-2) of RNase H1 with reported binding affinities ranging from 10 to 30 nM and IC50 values in a ribonuclease activity assay ranging from 50 to 100 nM (Pileur, et al., *Nucleic Acids Res.* 31: 5776-5788, 2003, which is incorporated herein by reference). Further, some aptamer-based inhibitors of RNAse may be determined using "The Ellington Lab Aptamer Database," sponsored by the University of Texas, and which can be located at http://aptamer.icmb.utexas.edu/index.php.

TABLE 2

RNase Inhibitors

| RNase Inhibitor | Ribonuclease |
|---|---|
| RNase Inhibitor protein | |
| Human placental RNase inhibitor (e.g., RNasin ®) | RNase A, RNase B, RNase C, Human placental RNase, RNase 5 (angiogenin) |
| SUPERase.In ™ RNase inhibitor | RNase A, RNase B, RNase C, RNase 1, RNase T1 |
| Rnase L inhibitor protein | RNase L |
| Rnase inhibitor small molecule | |
| oligo(vinylsulfonic acid) | RNase A |
| pdUppAp | RNase A, RNase 2, RNase 4 |
| 5'-diphosphoadenosine 3'-phosphate | RNase A, RNase 2, RNase 4 |
| 5'-diphosphoadenosine 2'-phosphate | RNase A, RNase 2, RNase 4 |
| Ap4A | RNase 2 |
| Ap5A | RNase 2 |
| 2'-fluoro-2'deoxyuridine 3'-phosphate | RNase A |
| arabinouridine 3'-phosphate | RNase A |
| 3'-N'alkylamino-3'-deoxy-arauridine | RNase A |
| Inosine 5'-phosphate | RNase A |
| 3'-N-oxyurea-3'-deoxythymidine 5'-phosphate | RNase Sa |
| 8-amino-5-(4'-hydroxybiphenyl-4-ylazo)naphthaline-2-sulfonate | RNase 5 (angiogenin) |
| epi-gallocatechin-3-gallate | RNase A |

Compounds Configured to Prevent Cleavage of at Least One Tissue RNA by a Ribonuclease Methods are provided which include administering at least one compound to an animal, wherein the at least one compound is configured to prevent the cleavage of at least one tissue RNA by a ribonuclease. In one aspect, the at least one compound is configured to bind to the at least one tissue RNA. The compound can be an oligonucleotide complementary to the at least one tissue RNA, e.g., a RNA, DNA, or PNA, or the compound can be a small molecule or an aptamer. In an embodiment, the compound can be an antisense oligonucleotide. In another embodiment, the compound can be a RNA binding protein or an anti-RNA antibody or an anti-RNase antibody. In a further aspect, the compound can be a ribonuclease binding molecule. Ribonucleic acid, for example, messenger RNA (mRNA), transfer RNA (tRNA), ribosomal RNA (rRNA), micro RNAs (miRNAs), small interfering RNAs (siRNAs), mitochondrial RNA, or a microbial pathogen RNA, can be stabilized by a class of proteins termed RNA-binding proteins (RBPs). See, for example, Ruvkun, Science 294: 797-799, 2001, which is incorporated herein by reference. In general, RBPs bind to distinct sequences within the mRNA and as such may alter the stability and translation rate, for example, of the bound mRNA. Some RBPs associate with RNA sequences that are widely expressed in mammalian mRNA such as, for example, the 5' cap structure (7-methylguanosine) or the 3' poly(A) tail. A distinct but heterogeneous group of RBPs associate with specific mRNA sequences frequently present in the 5' and 3' untranslated regions (UTRs) of the mRNA. An example are the ARE-binding proteins that bind to AU-rich elements in the UTRs of target mRNAs. AU-rich elements (AREs) are sequence elements of about 50 to about 150 nucleotides that are rich in adenosine and uridine bases and located at the 3' end of mRNAs. A number of ARE-binding proteins have been described such as, for example, AUF1, HuR/HuA, Hel-N1, HuC, HuD, TTP, DRF1, TIA-1, KSRP, CUG-BP2, nuclear factor 90 (NF90), nucleolin, TINI, and PAIP2. For a more extensive discussion of ARE-binding proteins and their effects on mRNA stability see, for example, Barreau, et al. Nucleic Acids Res. 33:7138-7150, 2005; Pullmann, et al., Mol. Cell. Biol. 27:6265-6278, 2007, which are incorporated herein by reference.

Antisense RNA Binding Compounds Administered to an Animal

Methods are provided which include administering at least one compound to an animal, wherein the at least one compound is configured to prevent the cleavage of at least one tissue RNA by a ribonuclease. In one aspect, the compounds are oligonucleotides that can have a sequence substantially complementary to at least a portion of the at least one tissue RNA. The oligonucleotide can form a double stranded RNA complex with the tissue RNA to stabilize the double-stranded complex for further analysis and quantification. In one aspect, the oligonucleotide can have a sequence substantially complementary to a 5' end or 3' end sequence of the at least one tissue RNA. In a further aspect, the oligonucleotide can have a sequence substantially complementary to a nuclease recognition sequence of the at least one tissue RNA. In an embodiment, the oligonucleotide can be antisense in its orientation.

Provided herein are oligonucleotides configured to bind RNA. The modulation can be effected through the targeting and stabilization of RNA. Strategies for designing antisense oligonucleotides are well described in the scientific and patent literature, and the skilled artisan can design such oligonucleotides using the techniques known to one skilled in the art and, as described herein. Antisense oligonucleotide technology has emerged as an important technique for manipulating gene expression. Synthetic antisense oligonucleotides are engineered complementary to a given messenger RNA (mRNA). By binding to the mRNA, the oligonucleotide prevents protein translation. This blockade may be mediated by RNAase-H degradation of the RNA-oligonucleotide complex. In addition to negative effects on protein translation, oligonucleotides may inhibit mRNA transcription through triple helix formation with complementary DNA regions. "Cardiac Cell and Gene Transfer: Principles, Protocols, and Applications," Methods in Molecular Biology, 219: 129-133, 2002, incorporated herein by reference. Thermodynamic criteria can be used to design antisense oligonucleotides having an improved hit rate in antisense screening studies. Matveeva, et al., Nucleic Acids Res., 31: 4989-4994. 2003. As a further example, gene walking/RNA mapping protocols to screen for effective antisense oligonucleotides are well known in the art, see, e.g., Ho, Methods Enzymol. 314: 168-183, 2000, describing a RNA mapping assay, which is based on standard molecular techniques to provide an easy and reliable method for potent antisense sequence selection. See also Smith, Eur. J. Pharm. Sci. 11: 191-198, 2000, each incorporated herein by reference.

Naturally occurring nucleic acids are used as antisense oligonucleotides. The antisense oligomers can be of any length; for example, in alternative aspects, the antisense oligomers are between about 5 to about 100 nucleotides, about 10 to about 80 nucleotides, about 15 to about 60 nucleotides, or about 18 to about 40 nucleotides in length. The optimal length can be determined by routine screening. The antisense oligonucleotides can be present at any concentration. The optimal concentration can be determined by routine screening. A wide variety of synthetic, non-naturally occurring nucleotide and nucleic acid analogues are known which can address this potential problem. For example, peptide nucleic acids (PNAs) containing non-ionic backbones, such as N-(2- aminoethyl)glycine units can be used. Antisense oligonucleotides having phosphorothioate linkages can also be used, as described in WO 97/03211; WO 96/39154; Mata, *Toxicol Appl Pharmacol.* 144: 189-197, 1997; *Antisense Therapeutics*, ed. Agrawal, Humana Press, Totowa, N.J., 1996. Antisense oligonucleotides having synthetic DNA backbone analogues provided by the invention can also include phosphorodithioate, methylphosphonate, phosphoramidate, alkyl phosphotriester, sulfamate, 3'-thioacetal, methylene(methylimino), 3'-N-carbamate, and morpholino carbamate nucleic acids, as described herein.

Formulation and Administration to an Animal of Pharmaceutical Compositions for Compounds Configured to Prevent Cleavage of at Least One Tissue RNA by a Ribonuclease Methods are provided that include administering at least one compound to an animal, wherein the at least one compound is configured to prevent the cleavage of at least one tissue RNA by a ribonuclease. Pharmaceutical compositions are provided comprising the at least one compound, which is a RNA stabilizing agent. The RNA stabilizing agent can be a ribonuclease binding molecule. Alternatively, a RNA stabilizing agent can be a compound which is configured to bind to the at least one tissue RNA. The RNA stabilizing agent can be administered alone or in combination with at least one other RNA stabilizing agent, or one or more pharmaceutically acceptable carriers, diluents, excipients, and/or vehicles such as, for example, buffers, surfactants, preservatives, solubilizing agents, isotonicity agents, and stablilizing agents as appropriate. A "pharmaceutically acceptable carrier" is an art-recognized term and includes a carrier that, for example, may be approved by a regulatory agency of the state and/or Federal government such as, for example, the United States Food and Drug Administration (US FDA); or is listed in the U.S. Pharmacopeia or other generally recognized pharmacopeia for use in animals, and more particularly in humans; or a pharmaceutically acceptable carrier may include equivalents of those described herein. Conventional formulation techniques generally known to practitioners are described in *Remington: The Science and Practice of Pharmacy*, 20$^{th}$ Edition, Lippincott Williams & White, Baltimore, Md., 2000, which is incorporated herein by reference.

Acceptable pharmaceutical carriers include, but are not limited to, the following: sugars, such as lactose, glucose and sucrose; starches, such as corn starch and potato starch; cellulose, and its derivatives, such as sodium carboxymethyl cellulose, ethyl cellulose, cellulose acetate, and hydroxymethylcellulose; polyvinylpyrrolidone; cyclodextrin and amylose; powdered tragacanth; malt; gelatin, agar and pectin; talc; oils, such as mineral oil, polyhydroxyethoxylated castor oil, peanut oil, cottonseed oil, safflower oil, sesame oil, olive oil, corn oil and soybean oil; polysaccharides, such as alginic acid and acacia; fatty acids and fatty acid derivatives, such as stearic acid, magnesium and sodium stearate, fatty acid amines, pentaerythritol fatty acid esters; and fatty acid monoglycerides and diglycerides; glycols, such as propylene glycol; polyols, such as glycerin, sorbitol, mannitol and polyethylene glycol; esters, such as ethyl oleate and ethyl laurate; buffering agents, such as magnesium hydroxide, aluminum hydroxide and sodium benzoate/benzoic acid; water; isotonic saline; Ringer's solution; ethyl alcohol; phosphate buffer solutions; other non-toxic compatible substances employed in pharmaceutical compositions.

Pharmaceutical compositions comprising one or more RNA stabilizing agents can be formulated in a pharmaceutically acceptable liquid carrier. The liquid carrier or vehicle can be a solvent or liquid dispersion medium comprising, for example, water, saline solution, ethanol, a polyol, vegetable oils, nontoxic glyceryl esters, and suitable mixtures thereof. The solubility of a chemical blocking agent can be enhanced using solubility enhancers such as, for example, water; diols, such as propylene glycol and glycerol; mono-alcohols, such as ethanol, propanol, and higher alcohols; DMSO (dimethylsulfoxide); dimethylformamide, N,N-dimethylacetamide; 2-pyrrolidone, N-(2-hydroxyethyl)pyrrolidone, N-methylpyrrolidone, 1-dodecylazacycloheptan-2-one and other n-substituted-alkyl-azacycloalkyl-2-ones and other n-substituted-alkyl-azacycloalkyl-2-ones (azones). The proper fluidity can be maintained, for example, by the formation of liposomes, by the maintenance of the required particle size in the case of dispersions or by the use of surfactants. One or more antimicrobial agent can be included in the formulation such as, for example, parabens, chlorobutanol, phenol, sorbic acid, and/or thimerosal to prevent microbial contamination. In some instances, one can include isotonic agents such as, for example, sugars, buffers, sodium chloride or combinations thereof.

Pharmaceutical compositions comprising one or more RNA stabilizing agents can be administered to an individual by any of a number of routes including, but not limited to, oral, nasal, pulmonary, rectal, transdermal, vaginal, or transmucosal routes as well as the parenteral routes. Suitable parenteral delivery routes for a RNA stabilizing agent include, but are not limited to, intramuscular, subcutaneous, intramedullary injections, as well as intrathecal, direct intraventricular, intravenous, intraperitoneal, intranasal, or intraocular injections.

In some instances, it may be appropriate to prevent the RNA stabilizing agent from entering cells. In the situation in which the RNA stabilizing agent is a protein such as a RNA inhibitor protein or a RNA binding protein, the size of the protein itself may preclude entry into a cell. In other situations, the RNA stabilizing agent can be covalently linked to an entity that is unlikely to transit the cellular membrane such as, for example, a protein of at least about 600 dalton, a hydrophilic agent, a microbead or nanoparticle. Examples of microbead and nanoparticle approaches and materials that would be appropriate for the delivery of one or more RNA stabilizing agent are described in *Nanomaterials for Medical Diagnosis and Therapy*, 1$^{st}$ edition, edited by Challa Kumar (Nanotechnologies for the Life Sciences Vol. 10, 2007, WILEY-VCH Verlag GmbH & Co. KGaA, Wienham, which is incorporated herein by reference).

The methods and compositions are further described with reference to the following examples; however, it is to be understood that the methods and compositions are not limited to such examples.

EXAMPLARY EMBODIMENTS

Example 1

A RNase inhibitor protein such as the human placental RNase inhibitor, for example, is used to stabilize extracellular RNA in vivo in preparation for ex vivo analysis of RNA transcripts associated with a malignancy such as, for example, malignant melanoma. Tyrosinase is an essential enzyme in the biosynthesis of melanin and is a useful diagnostic biomarker of melanoma (see, e.g., Boyle, et al., *Arch. Pathol. Lab. Med.* 126:816-822, 2002, which is incorporated herein by reference). Extracellular tyrosinase mRNA is detected in the serum of patients with malignant melanoma (see, e.g., Kopreski, et al., *Clin. Cancer Res.* 5:1961-1965, 1999, which is incorporated herein by reference) and as such may be used for diagnosis and monitoring of melanoma. A RNase inhibitor protein is administered to an animal prior to collection of a bodily fluid or tissue to prevent or modulate RNAse cleavage of extracellular tyrosinase mRNA, and to thereby stabilize extracellular tyrosinase mRNA and other melanoma associated mRNAs.

A subject is injected with a bolus of RNase inhibitor protein prior to collecting a bodily fluid for extraction of RNA. Alternatively, the RNase inhibitor protein is administered by infusion over some period of time. The RNase inhibitor protein is isolated from a natural source or generated using recombinant molecular biology techniques as described herein. The purified RNase inhibitor protein is administered to a subject by parenteral delivery such as, for example, subcutaneous, intramuscular, or intravenous injection. Parenteral delivery of a placenta-derived RNAse inhibitor protein to a mammal is described in U.S. Pat. No. 5,019,556, which is incorporated herein by reference.

Alternatively, the RNase inhibitor protein is administered in vivo in a retroviral expression vector (see, e.g., Wang, et al., *Angiogenesis*, 8:73-81, 2005, which is incorporated herein by reference). For example, cDNA corresponding to the human placental RNase inhibitor is retrieved by RT-PCR, subcloned into a retroviral vector such as pLNCX (BD Biosciences, San Jose, Calif.) and replicated in a mammalian packaging cell. Replicated retrovirons are shed into the cell culture medium and as such are purified from viral solution using centrifugation, filtration and size exclusion chromatography, for example, and injected into an individual. In vivo expression of the human placental RNase inhibitor by the retroviral vector is monitored using immunohistochemical and RT-PCR, for example.

The RNase inhibitor protein is administered as a single dose and a bodily fluid or tissue collected immediately or at a time in the future ranging from about 1 minute to about 24 hours, for example, depending upon the needs of the diagnostic test and the stability of the RNase inhibitor protein. Some proteins are relatively stable following in vivo administration. Serum stability of proteins can be modulated according to known methods, including, but not limited to, fusing the protein to a moiety that imparts stability, such as the Fc portion of an antibody. For example, the protein therapy Etanercept, a recombinant dimer of human soluble p75 TNF receptor fused to a Fc, has a half-life of 70 hours in humans (Madhusudan, et al., *Clin. Cancer Res.* 10:6528-6534, 2004, which is incorporated herein by reference). RNase inhibitor protein can be pegylated to improve serum half-life. Alternatively, multiple doses of the RNase inhibitor protein are administered over time.

A RNAse inhibitor (such as RNasin®) or RNA binding compound (such as an oligonucleotide), or both, are administered to an individual suspected of suffering from malignant melanoma. Whole blood is then collected from the individual in the absence of a coagulant and the serum isolated by centrifugation of the clotted blood at 830×g for 10 minutes. Total RNA is extracted from the serum samples using a commercial kit such as, for example, the PureLink Total RNA Blood Kit as described by the manufacturer (SKU# K1560-01, Invitrogen, Carlsbad, Calif.) and optionally treated with DNase I as described herein.

The RNA extracted from the serum is analyzed for the expression of a tumor marker associated with malignant melanoma such as tyrosinase, for example, using reverse transcription-PCR (RT-PCR) followed by gel electrophoresis (see, e.g., Kopreski, et al., *Clin. Cancer Res.* 5:1961-1965, 1999, which is incorporated herein by reference). For reverse-transcription, extracted RNA is incubated with dithiothreitol (0.01 M), random hexamer primers (100 pmol), deoxynucleotides (1 mM of each), magnesium chloride (4 mM), RNasin (25 units) and AMV reverse transcriptase (9 units) at room temperature for 10 minutes followed by incubated at 42° C. for 60 minutes. The resulting cDNA is subjected to 15-30 cycles of amplification in the presence of magnesium chloride (1.6 mM), dATP, dCTP, dGTP, and dTTP (200 uM each), PCR primers (2.5 pmol each), and Taq polymerase (1 unit). Exemplary forward and reverse primers for PCR amplification of tyrosinase are described in Kopreski, et al., (*Clin. Cancer Res.* 5:1961-1965, 1999, which is incorporated herein by reference). Alternative primers for amplification of tyrosinase or any other tumor marker may be designed based on the nucleotide sequence of the marker. The resulting PCR products are detected using gel electrophoresis. For example, the PCR products are chromatographed on a 1-4% agarose gel in 1× TBE (89 mM Tris-borate and 2 mM EDTA, pH 8.0) at 100 V for 2 hours and stained with ethidium bromide.

Alternatively, RNA is directly sequenced using Raman scattering as described in Deckert, Volker and Bailo, Elena. Tip-Enhanced Raman Spectroscopy of Single RNA Strands: Towards a Novel Direct-Sequencing Method. Angewandte Chemie International Edition. doi: 10.1002/anie.200704054, which is oincorporated herein by reference.

RNA encoding other melanoma markers may also be used to diagnose and monitor disease progression and therapy such as, for example, Melan A, Mage 3, bRAF oncogene, nRas oncogene, cyclin-dependent kinase (CDK) 4, CDKs cyclin D1 (CCND1), Rab38, CDK inhibitor 1A and 2A (p21, p16), BCL-6, Ki-67, $\alpha_v\beta_3$ integrin, ERK-1, ERK-2, CCR4, CCR7, CCR10, melastatin, MITF, galectin-3, β-catenin, IL-6 receptor, STAT1/STAT3, PTEN, AKT, TA90, osteopontin, MCAM, AP-2, CBP, FOXP3, CD3, CD4, TIA1, MDA-7, VEGFA, VEGFC, D2-40, HIF-1, CD9, TM4SF, and cKIT (see, e.g., Becker, et al., *Cancer Res.* 66:10652-10657, 2006, which is incorporated herein by reference).

Example 2

A small molecule RNase inhibitor such as a nucleotide analog, for example, is used to stabilize extracellular RNA in vivo in preparation for ex vivo analysis of RNA transcripts associated with a malignancy such as, for example, hepatocellular carcinoma. Hepatocellular carcinoma is one of the most common and fatal malignancies associated with hepatitis B and C viral infections. Extracellular human telomerase reverse transcriptase (hTERT) mRNA has been detected in patients with hepatocellular carcinoma and may be used to differentiate between other liver diseases such as liver cirrhosis and chronic hepatitis (Miura, et al., *Clin. Cancer. Res.* 11:3205-3209, 2005, which is incorporated herein by reference). As such, the small molecule RNase inhibitor may be administered to a patient with a liver disease to stabilize extracellular hTERT mRNA transcripts in a bodily fluid prior to analysis.

Suitable routes of administration of the small molecule RNase inhibitor include oral, rectal, transdermal, vaginal, or transmucosal routes as well as the parenteral administration routes described above. For example, the small molecule RNase inhibitor: 8-amino-5-(4'-hydroxylbiphenyl-4-ylazo) naphthalene-2-sulfonate is subcutaneously injected into the subject. See, for example, Kao, et al., *PNAS*, 99:10066-10071, 2002, which is incorporated herein by reference, where 40, 8, and 1.6 μg injections were administered once daily over the course of 35 days without overt toxicity to the animals.

As such, an individual with a liver disease is given a small molecule RNase inhibitor prior to collecting a bodily fluid for extraction of RNA. A single or multiple doses of a small molecule RNase inhibitor is administered depending, for example, upon the half-life of the small molecule RNase inhibitor and the length of time between first administration and ex vivo analysis. For example, in some instances it may be beneficial to allow 24 hours of exposure to the small molecule RNase inhibitor prior to ex vivo analysis. As such, if the half-life of the inhibitor is less than 24 hours the physician or other caregiver may chose to administer multiple doses of the small molecule RNase inhibitor.

At the time of analysis, blood or other bodily fluid is collected from an individual suspected of suffering from a liver disease. For example, blood is collected and serum isolated using a series of centrifugation steps (800×g with 0.45 µm filtration, 1,000×g, and 1,500×g) to eliminate lymphocyte cellular contamination as described by Miura, et al. (*Clin. Cancer. Res.* 11:3205-3209, 2005, which is incorporated herein by reference). Total RNA is extracted from the serum samples using TRI® Reagent RNA isolation reagent, for example, as described by the manufacturer (from, e.g., Sigma-Aldrich, St. Louis, Mo.) and optionally treated with DNase I as described herein.

The extracted RNA is analyzed using one of the many methods described herein. For example, the extracted RNA is subjected to quantitative reverse transcription-PCR (qRT-PCR) using appropriate primers to detect hTERT, for example, and other appropriate tumor markers and/or housekeeping genes. qRT-PCR primer sets for hTERT and α-fetoprotein (AFP), another conventional tumor marker used in clinical diagnosis of hepatocellular carcinoma, as well as for the housekeeping gene β2-microglobin have been described (see, e.g., Miura, et al., *Clin. Cancer. Res.* 11:3205-3209, 2005, which is incorporated herein by reference). The qRT-PCR reaction is carried out using a One Step RT-PCR kit (from, e.g., QIAGEN, Inc., Valencia, Calif.) in the presence of a DNA intercalating dye such as SYBR Green I (from, e.g., Sigma-Aldrich, St. Louis, Mo.) using a detection instrument: such as, for example, the ABI PRISM 7700 Sequence Detection System (from Applied Biosystems, Foster City, Calif.). The direct detection of PCR product is monitored in real-time by measuring the relative increase in fluorescence caused by the binding of SYBR Green I fluorescence to double-stranded DNA and is used to calculate the abundance of a specific RNA transcript in the RNA extract. As such, the relative abundance of extracellular hTERT and AFP mRNA extracted from individual with a liver disease is assessed and used to diagnose hepatocellular carcinoma.

Example 3

A RNA binding protein such as ELAV/HuR, for example, is used to stabilize extracellular RNA in vivo in preparation for ex vivo analysis of RNA transcripts associated with a malignancy. ELAV/HuR (embryonic lethal, abnormal vision/human R antigen) binds to and stabilizes mRNAs that contain adenosine/uridine rich elements (AREs) in their 3'-untranslated region. ELAV/HuR binds to a number of mRNA targets such as, for example, mRNAs encoding c-fos, MyoD, p21, cyclin A, cyclin B1, cyclin D1, NOSII/iNOS, GM-CSF, TNF-alpha, COX-2, IL-3, VEGF, and myogenin (see, e.g., Barreau, et al. *Nucleic Acids Res.* 33:7138-7150, 2005, which is incorporated herein by reference). A number of these ELAV/HuR binding mRNA species including c-fos, cyclin D1, VEGF, and COX-2, for example, are elevated in cancers. For example, COX-2 (cyclooxygenase-2), has been detected at increased levels in a variety of cancers including colon, gastric, and breast cancer (see, e.g., Denkert, *Modern Pathol.* 19:1261-1269, 2006; Mrena, et al., *Clin. Cancer. Res.* 11:7362-7368, 2005; Denkert, et al., *Clin. Canc. Res.* 10:5580-5586, 2004, which are incorporated herein by reference). As such, ELAV/HuR may be used to stabilize an extracellular mRNA such as COX-2 mRNA, for example, prior to analysis.

ELAV/HuR is expressed in a variety of mammalian tissues and cells and as such is isolated from a natural source using standard protein purification techniques. Alternatively, ELAV/HuR is generated using standard molecular biology techniques. The complete nucleotide coding sequence for human ELAV/HuR (Accession # U38175; NM_001419), for example, is found in the National Center for Biotechnology Information (NCBI) database (http://www.ncbi.nlm.nih-.gov/). cDNA corresponding to the coding sequence of ELAV/HuR is generated using PCR and standard molecular biology techniques. Alternatively, cDNA corresponding to ELAV/HuR is generated de novo using a custom gene synthesis service such as that provided by Blue Heron Biotechnology (Bothell, Wash.). Alternatively, full-length cDNA corresponding to the coding sequence of human ELAV/HuR is purchased from a commercial source (from, e.g., Origene, Rockville, Md., Cat. # RC201562). Once cloned, ELAV/HuR is expressed and purified using standard procedures.

An individual is injected with a pharmaceutically acceptable composition that includes a bolus of RNA binding protein such as ELAV/HuR, for example, prior to collecting a bodily fluid for extraction of RNA. Other means of administering the RNA binding protein to an individual may be used.

At the time of analysis, blood or other bodily fluid is collected from an individual and total RNA or poly(A)+ RNA extracted using methods described herein. RT-PCR is used to assess the expression of COX-2 mRNA or other mRNA species of interest. Primers for use in amplifying COX-2 sequence by PCR have been described (see, e.g., Uchida, et al., Clin. Cancer Res. 11:3363-3368, 2005, which is incorporated herein by reference). As such, COX-2 mRNA is used to diagnose and monitor individuals with cancer. For example, changes in the relative level of COX-2 has been correlated with positive response to chemotherapy in a subset of patients with colon cancer (see, e.g., Uchida, et al., Clin. Cancer Res. 11:3363-3368, 2005, which is incorporated herein by reference). Levels of COX-2 mRNA or other mRNA species of interest can also be determined by direct RNA sequencing.

Example 4

One or more RNA stabilizing agents such as a RNase inhibitor, a RNA binding protein or antibody, or a RNA binding oligonucleotide or PNA, for example, is used to stabilize RNA in vivo in preparation for ex vivo analysis of RNA transcripts associated with a malignancy or other pathological condition associated with the renal and urogenital track. The presence or absence of RNA in the urine may be indicative of a number of condition such as, for example, bladder cancer, kidney disease and kidney allograft rejection (see, e.g., Hanke, et al., *Clin. Chem.* 53:2070-2077, 2007; Kubo, et al., *Eur. J. Clin. Invest.* 29:824-826, 1999; Muthukumar, et al., *N. Engl. J. Med.* 353:2342-2351, 2005, which are incorporated herein by reference).

To assess RNA associated with urine, an individual is administered a RNA stabilizing agent and urine collected thereafter. A RNA stabilizing agent is administered to an individual by any of a number of means, including those as described herein. In some instances, the RNA stabilizing agent is injected directly into the bladder tissue with the aid of a cystoscope. Alternatively, the RNA stabilizing agent is directly infused into the bladder lumen using a catheter, for example. Urine is collected immediately or at some time point in the future.

RNA is isolated from urine and urine fractions using the methods described herein. For example, RNA in spontaneously voided urine or urine collected using a monovette, for example, is extracted by the addition of guanidinium thiocyanate to a final concentration of 3 mol/L in the presence of 0.025 mol/L sodium acetate and 0.25% N-lauroylsarcosine followed by phenol/chloroform extraction (see, e.g., Hanke, et al., *Clin. Chem.* 53:2070-2077, 2007, which is incorporated herein by reference). Alternatively, RNA is extracted from a urine cell pellet using the methods described herein. A urine cell pellet is generated by centrifugation of urine at 400×g for 5 minutes, for example. Alternatively, RNA is extracted from cell-free urine using the methods described herein. Cell-free urine is generated by passing voided urine through a 5 μm filter, for example.

One or more RNAs encoding biomarkers associated with bladder cancer may be used to diagnose and monitor the disease. Examples of biomarkers associated with bladder cancer include, but are not limited to, human complement factor H related protein (hCFHrp), nuclear matrix protein 22 (NMP-22), mucin glycoprotein, and carcinoembryonic antigen (CEA) (see, e.g., Grossman, et al., Urology, 67:62-64, 2006, which is incorporated herein by reference).

In some instances, the relative expression of two or more RNAs is used to diagnose and monitor bladder cancer and other diseases. Similarly, the relative expression of two or more RNAs is used to compare normal versus diseased individuals. For example, the relative expression of mRNAs encoding v-ets erythroblastosis virus E26 oncogene homolog 2 (ETS2) and urokinase plasminogen activator (uPa) correlates with the presence of bladder cancer (see, e.g., Hanke, et al., *Clin. Chem.* 53:2070-2071, 2007, which is incorporated herein by reference). For analysis, a RNA stabilizing agent is administered to an individual as described above. Urine is collected and RNA extracted from total urine, urine-cell pellets, and/or cell-free urine. The extracted RNA is subjected to RT-PCR using PCR primers for ETS2 and uPa as described by Hanke, et al. (*Clin. Chem.* 53:2070-2071, 2007, which is incorporated herein by reference). mRNA transcripts associated with housekeeping genes such as GAPDH, ribosomal protein large P0 (RPLP0), ubiquitin C, for example, and/or an external RNA standard such as, luciferase RNA, for example, are used to normalize RNA expression and account for intra-donor and interdonor variability. Analysis of RNA marker ratios is done using one or more readily available statistical analysis programs. For example, the ratio of ETS2 to uPa (ETS2/uPa) is positively correlated with bladder cancer tumor grade with higher ratios indicative of more advanced disease (Hanke, et al. (*Clin. Chem.* 53:2070-2071, 2007, which is incorporated herein by reference).

RNA extracted from urine can also be used to assess renal function and disease. For example, the Wilm's tumor suppressor gene WT1 is expressed in highly differentiated glomerular epithelial cells in the mature kidney. The presence of WT1 RNA in the urine is associated with inappropriate shedding of these cells and renal dysfunction and can be monitored using RT-PCR and WT1 specific primers (see, e.g., Kubo, et al., *Eur. J. Clin. Invest.* 29:824-826, 1999, which is incorporated herein by reference). Similarly, the presence of specific RNA species in urine such as FOXP3, for example, in the context of renal transplantation is indicative of acute rejection, rejection reversal, and/or graft failure (Muthukumar, et al., *N. Engl. J. Med.* 353:2342-2351, 2005, which is incorporated herein by reference). As such, one or more RNA stabilizing agents can be administered to an individual prior to analysis of RNA associated with renal dysfunction.

Example 5

One or more RNA stabilizing agents is given to an individual in conjunction with serial assessment of one or more RNAs in a bodily fluid or tissue to assess disease progression and/or response to therapy. For example, the levels of CEA and CA19-9 in patients with metastatic colorectal cancer decrease temporally in response to multiple treatment cycles with 5-fluorouracil and calcium folinate (see, e.g., Hanke, et al., *Annals Oncol.* 12:221-226, 2001, which is incorporated herein by reference). CEA levels can also be used for surveillance after curative tissue resection to monitor disease recurrence. As such, the baseline levels of a disease marker such as CEA and CA19-9 is determined at a first assessment point and subsequently reassessed over a period of time.

The first assessment point corresponds with the initiation of a course of treatment such as, for example, chemotherapy, radiation therapy, or drug therapy. Alternatively, the first assessment point corresponds with a point in time just prior to or just following resection of a tumor, for example, by surgery or laser therapy. The number and frequency of subsequent assessments is dictated by the length of treatment, the expected response time, the severity of the disease, and the likelihood of progression or recurrence. In some instances, reassessment over time demonstrates no change or an increase in the level of a RNA and indicates that the therapy or intervention is not working and alternative therapy should be considered. In some instances, the first assessment point occurs at a point in time prior to any indication of disease presence. Subsequent assessments are used to monitor for development of a disease, particularly in an individual or population of individuals at higher risk for a disease who might benefit from early therapeutic intervention.

One or more RNA stabilizing agents such as a RNase inhibitor or a RNA binding molecule is given to an individual prior to collecting bodily fluids and/or tissue for RNA extraction. RNA is extracted from a bodily fluid or tissue using the methods described herein. Real-time quantitative PCR, for example, is used to assess the level of specific disease markers. For example, the level of RNA encoding CEA is assessed using TaqMan real-time quantitative PCR and forward and reverse PCR primers as described by Godfrey et al., *Clin. Cancer Res.* 7:4041-4048, 2001, which is incorporated herein by reference. Additional tests such as a computed tomography (CT) scan, for example, can be used in conjunction with analysis of RNA encoding CEA to assess progression of colon cancer, for example.

Example 6

One or more RNA stabilizing agents is given to an individual prior to collecting cerebrospinal fluid (CSF) for assessment of one or more RNA associated with a neurological disorder. A neurological disorder can be a neurodegenerative disease such as Alzheimer's disease, Parkinson's disease, amyotrophic lateral sclerosis (ALS); a neuroinflammatory disease such as multiple sclerosis; a psychological disease such as schizophrenia, depression; a physical disease such as a stroke, head injury, for example.

Cerebrospinal fluid (CSF) is collected from an individual by means of a lumbar puncture in which a spinal needle is inserted between the lumbar vertebrae L3/L4 or L4/L5 and a small volume of fluid is extracted. RNA is extracted from the CSF using methods described herein. For example, a cell-free CSF supernatant is generated by centrifugation of CSF (400-600 microliters) at about 1,000×g for about 30 minutes at approximately 4° C. RNA is extracted from the cell-free CSF supernatant by the addition of guanidine isothiocyanate. Alternatively, the cell-free CSF supernatant is further centrifuged at about 100,000×g for about 60 minutes at approximately 4° C. to concentrate particulate-associated RNA in the high-speed pellet. RNA is extracted from the pellet using guanidine isothiocyanate and homogenization with sonication, dounce, or glass beads, for example.

The isolated RNA is be subjected to reverse transcription-PCR using target specific primers and the PCR products detected using the methods described herein. For example, human endogenous retroviral (HERV) RNA in the CSF is a useful marker of new-onset schizophrenia and as such HERV specific PCR primers are used for PCR to detect HERV RNA in the CSF as described by Karlsson, et al. (*Proc. Natl. Acad. Sci., USA.* 98:4634-4639, 2001, which is incorporated herein by reference).

Alternatively, the isolated RNA is subjected to PCR using a commercially available microarray specific for a given neurological disease such as, for example, Alzheimer's disease (see, e.g., Human Alzheimer's Disease RT$^2$ Profiler™ PCR Array: PAHS-057 SuperArray Bioscience Corporation, Frederick, Md.). In this instance, RNA is reverse transcribed, mixed with a reaction buffer and aliquoted into a microarray plate in which each well contains distinct primers for biomarkers associated with Alzheimer's. Real-time quantitative PCR is used to determine the expression level of various biomarkers potentially associated with Alzheimer's disease and associated neurogeneration such as, for example, beta-amyloid peptide; secretases such as ADAM9, APH1A, BACE1, BACE2, CTSB, NCSTN, PSEN1, PSEN2; peptidases involved in degradation of beta-amyloid peptide such as IDE, PLAT, PLAU, PLG; beta-amyloid clearance-associated proteins such as APLP1, APP, LRP1, LRP6, LRP8; other genes involved in beta-amyloid metabolism such as A2M, ACHE, APBB1, APBB2, APOE, BCHE, UBQLN1; genes associated with microtubule and cytoskeleton reorganization such as MAP2, MAPT, PKP4, PRKCI; genes involved in synapse formation such as APBA1, CHAT, BDNF; genes associated with cholesterol, lipid, and lipoprotein metabolism such as ABCA1, APOA1, CLU, HADH2, INS, LPL, SNCB; genes associated with apoptosis such as CASP3, CASP4, ERN1, PRKCA, PRKCE, IL1A, MPO, PRKCZ, SNCA, APPBP1, EP300; cell cycle regulator such as CDC2, CDK5, CDKL1; protein kinases such as GSK3A, GSK3B, INSR, PRKCB1, PRKCD, PRKCG, PRKCQ; cell signaling molecules such as APLP2, GNAO1, GNAZ, GNB1, GNB4, GNB5, GNG10, GNG11, GNG3, GNG4, GNG5, GNG7, GNG8, GNGT1, GNGT2; APBA3, PPBP1, GAP43, GNB2; and other genes involved in Alzheimer's disease such as UQCRC1, UQCRC2, CTSC, CTSD, CTSG, CTSL, UQCRC2, SERPINA3. An extensive microarray of this sort or others like it can also be used to compare the CSF-associated RNA from individuals with Alzheimer's disease, individuals with other neurological disorders, and normal individuals to more precisely delineate which RNA species are associated with specific neurological disorders.

Example 7

One or more RNA stabilizing agents is given to an individual in conjunction with assessing RNA collected from multiple bodily fluids and tissues. Sampling RNA from multiple sites is used, for example, to assess the spread or metastasis of cancerous cells that have migrated through the lymphatic vessels and vasculature from a primary tumor to a distant organ or tissue. The most common sites of metastasis from solid tumors are the lungs, bones, lymph node, liver and brain. (National Cancer Institute, FactSheet, Metastatic Cancer: Questions and Answers. www.cancer.gov/cancertopics/factsheet/Sites-Types/metastatic, 2004, which is incorporated herein by reference). Leukemia, multiple myeloma, and lymphoma, for example, are blood cancers but cells associated with these cancers may be found in lymph nodes, or other parts of the body such as liver or bones. Biomarkers are used to determine whether a solid tumor is a primary tumor or a metastatic tumor in that the biomarkers associated with the metastatic tumor will reflect the primary tumor origin. For example, biomarkers for breast cancer such as Bcl-2 and epidermal growth factor (EGF) receptor are detected in brain metastases (see, e.g., Weil, et al., *Am. J. Pathol.* 167:913-920, which is incorporated herein by reference).

The diagnosis and monitoring of other diseases can be performed using one or more RNA stabilizing agent in conjunction with collecting RNA from multiple sites. For example, chronic kidney disease is associated with low grade inflammation and changes in the composition of the urine. As such, an individual with chronic kidney disease is treated with one or more RNA stabilizing agent followed by collection of blood, urine and a kidney biopsy, for example, all of which are analysed for biomarker RNAs or specific miRNA profiles, for example. Similarly, diabetes is a progressive disease associated with increasing prevalence over time of neuropathy, retinopathy, nephropathy and micro and macrovascular dysfunctions (see, e.g., Gedela, et al., *Int. J. Biomed. Sci.* 3:299-236, 2007, which is incorporated herein by reference). As such, RNA samples are taken from multiple sites such as, for example, blood, urine, aqueous humor, cerebrospinal fluid and tissue biopsies to assess the degree of diabetes-induced pathologies. For example, mRNA encoding rhodopsin, an important protein in visual function, can be detected in RNA isolated from blood and increases in concentration with the extent of diabetic retinopathy (see, e.g., Hamaoui, et al., *Clin. Chem.* 50:2152-2155, 2004, which is incorporated herein by reference).

Example 8

A RNA stabilizing agent is given to a patient in conjunction with assessing microRNA (miRNA) from bodily fluids and tissue. miRNA has been implicated in a number of processes associated with cancer including oncogenic activity, tumor suppressor activity, tumor invasion and metastasis (see, e.g., Sassen et al. *Virchows Arch.* 452:1-10, 2008, which is incorporated herein by reference). Nucleotide sequence for over 400 human miRNAs have been described and are readily accessable (see, e.g., www.microRNA.org; Betel, et al., *Nucleic Acids Res.* 36:(database issue)D149-D153, 2008, which is incorporated herein by reference).

miRNA is isolated from a bodily fluid or tissue using one or more of the methods described herein such as, for example, the guanidine isothiocyanate/phenol:chloroform extraction method. Alternatively, miRNA is isolated using a commercially available isolation kit such as, for example, mirPremier™microRNA Isolation Kit (Sigma-Aldrich, St. Louis, Mo.), mirVana™ miRNA Isolation Kit (Applied Biosystems, Foster City, Calif.), and PureLink™ miRNA Isolation Kit (Invitrogen, Carlsbad, Calif.). Isolated miRNA is subsequently used for hybridization and PCR applications.

miRNA expression profiling can be used to assess the relative expression of miRNAs in association with cancer or other disease state. Profiling miRNA of normal and diseased individuals can be used to establish a pattern of expression suggestive of a given disease. In addition, changes in the miRNA profile over the course of a disease can be correlated with response to therapy, disease progression and/or recurrence. This approach can also establish very specific miRNAs as biomarkers of specific disease states.

miRNA profiling is performed with RNA isolated from normal and diseased bodily fluids and tissues using oligonucleotide microarrays (see, e.g., Barad, et al., *Genome Res.* 14:2486-2494, 2004, which is incorporated herein by reference). In this instance, oligonucleotides corresponding to the over 400 human miRNA sequences in the microRNA database described above, for example, is used to develop a custom microarray (see, e.g., Agilent Technologies, Santa Clara, Calif.). Total RNA is isolated from a bodily fluid or tissue using the methods described herein. In some instance, the RNA is further size-fractioned to isolate small RNA fragments using, for example, an YM-100 column (Millipore Corporation, Billerica, Mass.). The size-fractionated RNA is ligated with an adapter sequence to facilitate reverse transcription and PCR amplification to generate cDNA (see, e.g., Barad, et al., *Genome Res.* 14:2486-2494, 2004, which is incorporated herein by reference). The pool of cDNAs is transcribed back to RNA in the presence of a fluorescent nucleotide such as, for example, cyanine 3-CTP or cyanine 5-CTP and hybridized to the oligonucleotide microarray containing miRNA sequences. The intensity of hybridized fluorescence correlates with the relative abundance of a given miRNA in the total RNA extracted from a bodily fluid or tissue.

Alternatively, real-time PCR in a multiwell format is used for miRNA profiling. For example, profiling miRNA isolated from individuals with cancer, for example, is done using a commercially available PCR array (see, e.g., Human Cancer RT$^2$ miRNA PCR Array: MAH-102, from SuperArray Bioscience Corporation, Frederick, Md.). In this instance, the miRNA is polyadenylated at the 3 prime end of the sequence and reverse transcribed using a universal primer that includes oligo(dT). The resulting cDNA is aliquoted into a microarray plate in which each well contains a 5' primer specific for a given miRNA and the universal primer. Real-time quantitative PCR is then carried out and the relative expression of any given miRNA in the original RNA sample determined.

Each recited range includes all combinations and sub-combinations of ranges, as well as specific numerals contained therein.

All publications and patent applications cited in this specification are herein incorporated by reference to the extent not inconsistent with the description herein and for all purposes as if each individual publication or patent application were specifically and individually indicated to be incorporated by reference for all purposes.

The herein described components (e.g., steps), devices, and objects and the description accompanying them are used as examples for the sake of conceptual clarity and that various configuration modifications using the disclosure provided herein are within the skill of those in the art. Consequently, as used herein, the specific exemplars set forth and the accompanying description are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural or singular terms herein, those having skill in the art can translate from the plural to the singular or from the singular to the plural as is appropriate to the context or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable", to each other to achieve the desired functionality. Specific examples of operably couplable include but are not limited to physically mateable or physically interacting components or wirelessly interactable or wirelessly interacting components or logically interacting or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an"; the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not limited to systems that have A alone, B alone, C alone, A and B together, A and C together, B and C together, or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The various aspects and embodiments disclosed herein are for purposes of illustration and are not intended to be limiting, with the true scope and spirit being indicated by the following claims.

What is claimed is:

1. A method of diagnosing disease in an animal comprising:
    administering at least one compound to an animal wherein the at least one compound is able to prevent the cleavage of at least one tissue RNA by a ribonuclease, wherein the at least one compound is an RNA binding protein able to bind to at least one tissue RNA,
    collecting a sample of at least a portion of blood or tissue containing the at least one tissue RNA from the animal, and
    determining at least one characteristic of the at least one tissue RNA in the collected sample from the animal as a diagnostic indicator of a physiological state of the animal.

2. The method of claim 1, wherein the administering at least one compound occurs within a defined time before the collecting of the sample.

3. The method of claim 1, wherein the at least one compound is a ribonuclease binding molecule.

4. The method of claim 1, wherein the at least one compound is an oligonucleotide molecule having a sequence substantially complementary to the nucleotide sequence of the at least one tissue RNA.

5. The method of claim 1, wherein the at least one compound is an oligonucleotide molecule having a sequence substantially complementary to at least a portion of the at least one tissue RNA.

6. The method of claim 5, wherein the at least one compound is an oligonucleotide molecule having a sequence substantially complementary to a 5' end or 3' end sequence of the at least one tissue RNA.

7. The method of claim 5, wherein the at least one compound is an oligonucleotide molecule having a sequence substantially complementary to a nuclease recognition sequence of the at least one tissue RNA.

8. The method of claim 4, wherein the at least one compound is a RNA.

9. The method of claim 4, wherein the at least one compound is a DNA.

10. The method of claim 4, wherein the at least one compound is a PNA.

11. The method of claim 1, wherein the at least one compound is an aptamer.

12. The method of claim 1, wherein the at least one tissue RNA is from whole blood, blood plasma, serum, urine, effusions, ascites, saliva, cerebrospinal fluid, cervical secretions, endometrial secretions, semen, gastrointestinal secretions, bronchial secretions, breast fluid, or organ tissue.

13. The method of claim 1, wherein the at least one tissue RNA is mRNA.

14. The method of claim 1, wherein the at least one tissue RNA is transfer RNA or ribosomal RNA.

15. The method of claim 1, wherein the at least one tissue RNA is microRNA.

16. The method of claim 1, wherein the at least one tissue RNA is mitochondrial RNA.

17. The method of claim 1, wherein the at least one tissue RNA is pathogen RNA.

18. The method of claim 17, wherein the pathogen RNA is from bacteria, virus, or parasite.

19. The method of claim 1, wherein the at least one characteristic is a level of the at least one tissue RNA in the collected sample.

20. The method of claim 19, further comprising comparing the level of the at least one tissue RNA in the collected sample from the animal to a level of the at least one tissue RNA in a collected sample of an animal in a reference state.

21. The method of claim 19, further comprising determining the presence of a disease in the animal by comparing the level of the at least one tissue RNA in the collected sample from the animal to a level of the at least one tissue RNA in a collected sample of an animal in a non-diseased state.

22. The method of claim 21, wherein the disease is cancer or infectious disease.

23. The method of claim 21, wherein the disease is atherosclerotic disease.

24. The method of claim 1, wherein the at least one characteristic is an identity of the at least one tissue RNA.

25. The method of claim 1, wherein the at least one characteristic is an identity of the at least one tissue RNA associated with a disease state.

26. The method of claim 25, wherein the disease state is infectious disease, cancer, or atherosclerosis.

27. The method of claim 1, wherein the at least one characteristic is a relative level of at least two different RNAs.

28. The method of claim 1, wherein the at least one characteristic is a relative level of at least two different RNAs associated with a disease state.

29. The method of claim 1, wherein the at least one characteristic is a relative level of at least two different RNAs measured in two different tissues in the animal.

30. The method of claim 1, wherein the at least one characteristic is a relative level of at least two different RNAs measured at two different locations in the animal.

31. The method of claim 1, wherein the at least one characteristic is a relative level of the at least one tissue RNA measured at two or more time points.

32. The method of claim 3, further comprising administering a compound able to bind to the at least one tissue RNA.

33. The method of claim 3, wherein the ribonuclease binding molecule is able configured to prevent transport of the ribonuclease binding molecule across a cell membrane.

34. The method of claim 33, wherein the ribonuclease binding molecule is bound to a bead.

35. The method of claim 33, wherein the ribonuclease binding molecule is joined to a hydrophilic moiety.

36. The method of claim 33, wherein the ribonuclease binding molecule has a molecular weight of at least about 600 daltons.

37. The method of claim 3, wherein the ribonuclease binding molecule is a polypeptide inhibitor of ribonuclease.

38. The method of claim 3, wherein the ribonuclease binding molecule is an antibody to ribonuclease.

39. The method of claim 3, wherein the ribonuclease binding molecule is an aptamer to ribonuclease.

40. The method of claim 37, wherein the ribonuclease binding molecule is RNasin.

41. The method of claim 37, wherein the ribonuclease binding molecule is a human placental inhibitor.

42. The method of claim 1, wherein the animal is human.

43. The method of claim 1, wherein the at least one tissue RNA is released from a cell that is undergoing or has undergone apoptosis.

44. The method of claim 1, wherein the RNA binding protein is an anti-RNA antibody.

* * * * *